US007943304B2

(12) United States Patent
Vallabhaneni

(10) Patent No.: US 7,943,304 B2
(45) Date of Patent: May 17, 2011

(54) METHOD AND APPARATUS FOR CHROMOSOME PROFILING

(76) Inventor: Ramesh Vallabhaneni, Orlando, FL (US)

( * ) Notice: Subject to any disclaimer, the term of this patent is extended or adjusted under 35 U.S.C. 154(b) by 681 days.

(21) Appl. No.: 11/034,085

(22) Filed: Jan. 12, 2005

(65) Prior Publication Data

US 2006/0154263 A1 Jul. 13, 2006

(51) Int. Cl.
*C12Q 1/68* (2006.01)
*G01N 33/53* (2006.01)
*C12P 19/34* (2006.01)
*C07H 21/02* (2006.01)
*C07H 21/04* (2006.01)

(52) U.S. Cl. ........... 435/6; 435/7.1; 435/91.1; 536/23.1; 536/24.3

(58) Field of Classification Search ............. 435/6, 91.1, 435/183, 283.1, 287.1, 287.2, 7.1; 436/94, 436/501; 536/23.1, 24.3, 24.33, 25.3
See application file for complete search history.

(56) References Cited

U.S. PATENT DOCUMENTS

| | | | |
|---|---|---|---|
| 6,051,835 | A | 4/2000 | Pettipiece et al. |
| 6,066,459 | A | 5/2000 | Garini et al. |
| 6,136,540 | A | 10/2000 | Tsipouras et al. |
| 6,203,977 | B1 | 3/2001 | Ward et al. |
| 6,221,607 | B1 | 4/2001 | Tsipouras et al. |
| 6,255,465 | B1 | 7/2001 | Ferguson-Smith et al. |
| 6,270,971 | B1 | 8/2001 | Ferguson-Smith et al. |
| 6,280,929 | B1 | 8/2001 | Gray et al. |
| 6,335,167 | B1 | 1/2002 | Pinkel et al. |
| 6,344,315 | B1 | 2/2002 | Gray et al. |
| 6,500,612 | B1 | 12/2002 | Gray et al. |
| 6,524,798 | B1 | 2/2003 | Goldbard et al. |
| 6,596,479 | B1 | 7/2003 | Gray et al. |
| 6,607,877 | B1 | 8/2003 | Gray et al. |

OTHER PUBLICATIONS

Attached definition for "marker chromosome" from Wikipedia, the free encyclopedia.*
The defintion of "Robertsonian translocation" from Wikipedia, the free encyclopedia. Printed on Mar. 24, 2010.*
The definition for "Marker chromosome" from hganj.org/Glossary.htm. Printed on Sep. 17, 2010.*
Van Rooijen et al., Double immunocytochemical staining in the study of antibody-producing cells in vivo., Immunology 51:417-421 (1984).
Van Rooijen et al. double immunocytochemical staining in the study of antibody-producing cells in vivo, J. of Histochemistry and Cytochemistry 33:3:175-178 (1985).
Claassen et al., Double enzyme conjugates, producing an intermediate color, for silultaneous and direct detection of three difference intracellular immunoglobulin determinants with only two enzymes, J. of Histochemistry and Cytochemistry 34:4:423-428 (1986).
Telenius et al., Degenerate oligonucleotide-primed PCR: general amplification of target DNA by a single degenerate primer, Genomics 13:718-725 (1992).
Bailey et al., Coincidence painting: a rapid method for cloning region specific DNA sequences, Nucleic Acids Research 21:22:5117-5123 (1993).
Cheung et al., Whole genome amplification using a degenerate oligonucleotide primer allows hundreds of genotypes to be performed on less than one nanogram of genomic DNA, Proc. Nat'l Acad. Sci. USA 93:14676-14679 (1996).
Craig et al., Removal of repetitive sequences from FISH probes using PCR-assisted affinity chromatography, Hum. Genet. 100:472-476 (1997).
Davison et al., Subtracted, unique-sequence, in situ hybridization experimental and diagnostic applications, Am. J. of Pathology 153:1401-1409 (1998).
Reed et al., Demonstration of Kaposi's Sarcoma-associated Herpes Virus Cyclin-D homolog in cutaneous Kaposi's Sarcoma by colorimetric in situ hybridization using a catalyzed signal amplification system, Blood 91:10:3825-3832 (1998).
Pitard et al., Structural characteristics of supramolecular assemblies formed by guanidinium-cholesterol reagents for gene transfection, Proc. Nat'l Acad. Sci. USA 96:2621-2626 (1999).
Schermelleh et al., Laser microdissection and laser pressure catapulting for the generation of chromosome specific paint probes, BioTechniques 27:362-367 (1999).
Kasai et al., Detection of SYT-SSX fusion transcripts in both epithelial and spindle cell areas of biphasic synovial sarcoma using laser capture microdissection, J. Clin. Pathol.: Mol. Pathol. 53:107-110 (2000).
Nishikawa et al., Hepatocyte-targeted in vivo gene expression by intravenous injection of plasmid DNA complexed with synthetic multi-functional gene delivery system, Gene Therapy 7:548-555 (2000).
Hirose et al., Tissue microdissection and degenerate oligonucleotide primed-polymerase chain reaction (DOP-PCR) is an eleffective method to analyze genetic abberations in invasive tumors, J. of Molecular Diagnostics 3:2:62-67 (2001).
Marchio et al., Chromosomal abnormalities in liver cell dysplasia detected by comparative genomic hybridisation, J. Clin. Pathol.: Mol. Pathol. 54:270-274 (2001).
Grosse et al., Intracellular rate-limiting steps of gene transfer using glycolsylated polylysines in cystic fibrosis airway epithelial cells, Gene Therapy 9:1000-1007 (2002).
Kubickova et al., The use of laser microdissection for the preparation of chromosome-specific painting probes in farm animals, Chromosome Research 10:571-577 (2002). Stark et al., Combined nanomanipulation by atomic force microscopy and UV-laser ablation for chromosomal dissection, Eur. Biophys. J. 32:33-39 (2003).
Cardoso et al., Genomic profiling by DNA amplification of laser capture microdissected tissues and array CGH, Nucleic Acids Research 32:19:e146 (2004). Hobza et al., FAST-FISH with laser beam microdissected DOP-PCR probe distinguishes the sex chromosomes of *Silene latifolia*, Chromosome Research 12:245-250 (2004).
Thalhammer et al., Generation of chromosome painting probes from single chromosomes by laser microdissection and linker-adaptor PCR, Chromosome Research 12:337-343 (2004).
Yasuda et al., Restricted cytokine production from mouse peritoneal macrophages in culture in spite of extensive uptake of plasmid DNA, Immunology 111:282-290 (2004).
Meuwissen, et al., Colocalization of intraplaque C reactive protein, complement, oxidised low density lipoprotein, and macrophages in stable and unstable angina and acute myocardial infarction, J. Clin. Pathol. 59:196-201 (2006).

* cited by examiner

*Primary Examiner* — Frank W Lu
(74) *Attorney, Agent, or Firm* — Akerman Senterfitt

(57) ABSTRACT

A method and apparatus for generating an Interphase chromosome profile. The method comprises obtaining a sample containing cells having chromosomes for profiling; obtaining species specific DNA probes, wherein the DNA probes are capable of marking at least one chromosome at substantially equidistant locations on said chromosome; hybridizing the sample with the DNA probes; using a plurality of enzymes to produce differential color bands on the chromosome for colorimetric analysis of the sample; and using visual analysis for determining the profile of the chromosome.

40 Claims, 19 Drawing Sheets
(16 of 19 Drawing Sheet(s) Filed in Color)

METHOD AND APPARATUS FOR CHROMOSOME PROFILING

FIELD OF THE INVENTION

The subject invention pertains to the field of cytogenetics, more particularly to chromosomal profiling.

BACKGROUND OF THE INVENTION

Cytogenetics is the field of study of chromosomes during the metaphase stage of the cell life cycle. It is at this stage where chromosomes are at their highest point of condensation and are most convenient to study in both the normal and disease state. Currently the most frequently used technique in the cytogenetics field (worldwide) is either short term (<10 days) or long term (up to 45 days) culture of the specimen submitted for testing. Specimens comprise a number of varying types such as peripheral blood, bone marrow, amniotic fluid, solid tissue, products of conception, pleural effusion and the like. After successful culture, through various processes, metaphase chromosomes are generally obtained and read, to determine whether the individual tested has a genetic abnormality. This process is quite complex and requires the use of numerous chemicals and reagents as well as a significant amount of time and expertise.

Chromosomal studies are frequently requested for various diagnostic purposes including the following: 1) prenatal diagnosis; 2) Peripheral blood chromosome test (to test for patients with abnormal phenotypic features, mental retardation, couples with infertility issues as well as multiple miscarriage issues to determine whether the cause is genetic; 3) Leukemia/Lymphoma diagnosis (vital to both accurate diagnosis as well as management of drug protocols); and 4) solid tumor diagnosis and treatment management (for cancers including bladder, prostate, kidney, breast, lung and the like.

For nearly fifteen years, a technique called Fluorescent In Situ Hybridization (FISH) has been used to obtain the chromosome/karyotype information. This technique, however, is limited. Utilizing the FISH technique, complete karyotype information cannot be obtained. A significant amount of the FISH testing has been used on Interphase stage nuclei, where chromosomes are not visible by the routine cytogenetic techniques, without further culture. Recently, a more complete chromosomal analysis, or karyotype information, was possible using the multiplex FISH (M-FISH) technique. The problem with this technique was that one culture was still required to obtain chromosomes for testing. Only then could M-FISH clarify suspected abnormalities as well as detect new or unsuspected changes.

Even more recently, several multicolor banding techniques, such as multicolor banding (MCG), multicolor chromosome bar code technique, cross-species color banding technique (rx-FISH), spectral color banding technique (SCAN) were developed. Of all of these techniques, only MCG has been applied to Interphase chromosomes.

Most FISH-based techniques use disease-specific probes. When disease-specific probes are generated, the probe sets are limited to the existing knowledge of specific alterations such as translocations, deletions, inversions, amplifications or other known chromosomal anomalies. Without previous knowledge of a suspected genetic abnormality, Cytogeneticists were unable to make a diagnosis for an unknown or unsuspected genetic disorder. Utilizing whole chromosome paints, allows previously undetected translocations to be recognized. This, however, is a very cumbersome process and required the use of twenty-four (24) separate chromosome painting probe set. Furthermore, the process yields information only on a single type of genetic abnormality, namely, a translocation between two different chromosomes. Often in disease processes, genetic alterations comprise numerous manifestations including translocations, deletions or inversions. These other changes, especially, intrachromosomal changes cannot all be detected by current chromosome painting probe sets. Instead, they require yet another set or multiple sets of disease specific probes thereby becoming cost-prohibitive for the routine clinical cytogenetics laboratory.

Numerous additional draw backs exist with the above mentioned techniques, for studying the metaphase chromosomes, these include: very complex color banding patterns obtained to recognize individual human chromosomes; techniques that require the use of very expensive equipment such as filters, dichroic mirrors, CCD cameras, sophisticated computer software, inferometers and other specialized apparatus to interpret banding patterns; techniques that do not provide complete karyotype information, i.e., the detection of certain type of abnormalities, such as, Robertsonian translocations; each of the techniques are fluorochrome-based, wherein the fluorescence quenches or fades and the resulting banding pattern is not permanent; resulting banding patterns that are assigned psuedo-colors through the use of by computer software and cannot be interpreted by simple human observation; techniques, that while useful in a research setting, are not practical for routine use in clinical cytogenetics laboratories; and marker chromosomes that are structurally altered and generally cannot be traced, this is especially critical as marker chromosomes have both diagnostic as well as prognostic implications in numerous clinical situations.

One genetic abnormality is of particular importance in genetic diagnosis, this abnormality is referred to as a Robertsonian translocation. Robertsonian translocations are translocations between acrocentric chromosomes that join by their centromeres, resulting in one less centromere in the karyotype. Robertsonian transolocations are clinically significant particularly in prenatal diagnosis. A pathological condition called Uniparental Disomy (UPD) exists for chromosomes 13, 14, and 15. UPD in the fetus, detected in the prenatal diagnosis, contributes to severe clinical manifestations and significantly adds to infant morbidity rates.

The documents and publications cited in this disclosure are incorporated herein by reference in their entirety, to the extent they are not inconsistent with the explicit teachings set forth.

BRIEF SUMMARY OF THE INVENTION

Accordingly, it is an object of the present invention to provide a method and apparatus for chromosome profiling.

Aspects of the present invention include a method for generating an Interphase chromosome profile including obtaining a sample containing cells having chromosomes for profiling; obtaining species specific DNA probes, the DNA probes capable of marking at least one chromosome at substantially equidistant locations on the chromosome; hybridizing the sample with the DNA probes; using a plurality of enzymes to produce differential color bands on the chromosome for colorimetric analysis of the sample; using visual analysis for determining the profile of the chromosome based on the colorimetric analysis.

The method further contemplates in situ hybridization. In an exemplary embodiment the in situ hybridization can occur on a slide. The slide can, for example, comprise a series of wells for receiving, hybridizing and analyzing said DNA profile.

In another aspect of the present invention, the visual analysis means can include a light microscope or CCD camera.

Aspects of the invention contemplate obtaining testing samples from amniotic fluid; peripheral blood; plural fluid; bone marrow; tumor tissue; products of conception or any other source containing cells having chromosomes for analysis.

The method according to aspects of the invention include visual detection of a chromosonal abnormality, such as, for example, a translocation, or more specifically, a Robertsonian translocation.

The method according to aspects of the invention contemplates yielding a complete karyotype.

The invention also includes a method of colorimetric in situ hybridization including the steps of: obtaining a sample containing cells having chromosomes for profiling; obtaining species specific DNA probes, capable of marking chromosome at substantially equidistant locations on the chromosome; in situ hybridizing the sample with the DNA probes; using a plurality of enzymes to produce differential color bands on the chromosome for colorimetric analysis; and using visual analysis for determining the profile of said chromosome.

The method can further include the step of in situ hybridizing the sample on a slide, wherein the slide includes a series of wells for receiving, hybridizing and analyzing said DNA profile.

The invention can also include a method of visually detecting Robertsonian translocations in chromosomes comprising the steps of: obtaining a sample containing cells having chromosomes for profiling; obtaining human DNA probes, capable of marking at least two chromosomes at substantially equidistant locations on each of the chromosomes; hybridizing the sample with said DNA probes; using a plurality of enzymes to produce differential color bands on the chromosomes for colorimetric analysis; and using visual analysis to determine whether a Robertsonian translocation has occurred between said chromosomes.

According to the invention, the method can also include hybridizing the sample in situ on a slide that includes a series of wells for receiving, hybridizing and analyzing said DNA profile. This method can also include visual analysis utilizing a light microscope or a CCD camera.

The method also contemplates a DNA sample wherein the origin of the sample is selected from the group consisting of: amniotic fluid; peripheral blood; plural fluid; bone marrow; tumor tissue; and products of conception.

In an additional embodiment of the present invention, a method of detecting marker chromosomes includes the steps of: obtaining a sample containing cells having chromosomes for profiling; obtaining human DNA probes, said DNA probes capable of marking at least two chromosomes at substantially equidistant locations on each of the chromosomes; hybridizing said sample with the DNA probes; and using a plurality of enzymes to produce differential color bands on the chromosomes for colorimetric analysis of the chromosomes.

The method for detecting marker chromosomes can include the in situ hybridization of the sample on a slide including a series of wells for receiving, hybridizing and analyzing the DNA profile. The detection can be done by visual analysis utilizing a light microscope or CCD camera.

The DNA sample for detection can originate from one of the following: amniotic fluid; peripheral blood; plural fluid; bone marrow; tumor tissue; and products of conception.

Another aspect of the present invention contemplates a method of labeling a chromosome including the steps of: obtaining a sample containing cells having chromosome for labeling, obtaining species specific DNA probes, wherein the DNA probes can be capable of labeling the chromosome at substantially equidistant locations, hybridizing the chromosome with the DNA probes, wherein the chromosome is labeled.

The method can include the in situ hybridization of the chromosome on a slide, wherein the slide includes a series of wells for receiving, hybridizing and analyzing the DNA profile. The method further contemplates a DNA origin selected from the group consisting of: amniotic fluid; peripheral blood; plural fluid; bone marrow; tumor tissue; and products of conception.

In an exemplary embodiment according to aspects of the present invention includes a kit for Interphase chromosome profiling, a plurality of species specific DNA probes, wherein the DNA probes can be capable of marking at least one chromosome at substantially equidistant locations on the chromosome, a plurality of enzymes for producing differential color bands on the chromosome for colorimetric analysis and a plurality of slides for in situ hybridizing the chromosome with the probe set.

The kit can further include a visual analysis means for the colorimetric analysis of the one chromosome, such as, for example, a microscope, or a camera.

Another embodiment according to aspects of the present invention includes a probe set including a plurality of species specific DNA probes, wherein the DNA probes can be designed to mark at least one chromosome at substantially equidistant locations on the chromosome. The probe set can further include a plurality of enzymes for producing colored bands on said chromosome. A further embodiment, according to aspects of the invention includes a slide for in situ Interphase chromosome hybridization having a glass slide further having a plurality of wells wherein in situ hybridization can occur.

The foregoing describes a method of obtaining a chromosome profile using Interphase Chromosome Profiling (ICP), to obtain the complete chromosome and karyotype information from any cell/specimen type without need for additional tissue culturing. This is accomplished by combing proprietary DNA probe sets and CISH technologies on Interphase nuclei. Utilizing the methods disclosed herein, approximately 99% of all chromosome abnormalities can be detected, and results generated with a turn around time (TAT) of less than 48 hours The invention relates to methods and apparatus for obtaining complete human karyotype information by observing individual human chromosomes in Interphase cells in hybridization chambers on a plurality of slides. ICP requires no prior knowledge of the presence of specific or suspected diseases, detects known and unknown genetic changes, and provides a complete karyotype in a single test. Moreover, ICP requires no cell culture and provides a detection mechanism for nearly all types of chromosome changes in Interphase nuclei.

Further objects and advantages of the present invention will become apparent by reference to the following detailed disclosure of the invention and appended drawings wherein like reference numerals refer to the same feature, component or element.

BRIEF DESCRIPTION OF THE DRAWINGS

The patent or application file contains at least one drawing and/or photomicrograph executed in color. Copies of this patent or patent application publication with color drawing(s) will be provided by the Office upon request and payment of the necessary fee.

DESCRIPTION OF THE PREFERRED EMBODIMENT

Figure 1A:
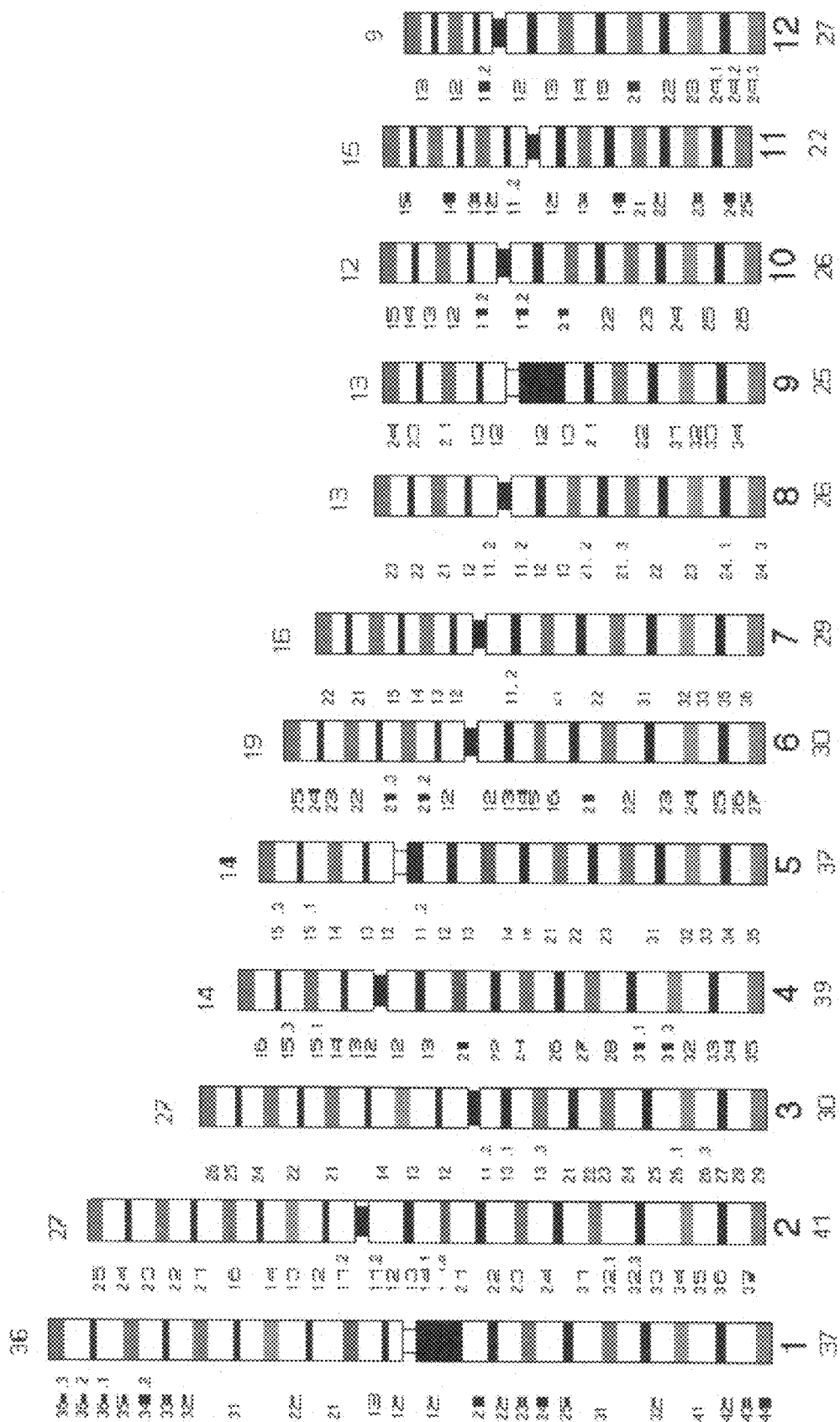
FIGS. 1a and 1b are Interphase Chromosome Profile ideograms illustrating exemplary resulting color bands according to aspects of the present invention.
Figure 1B:
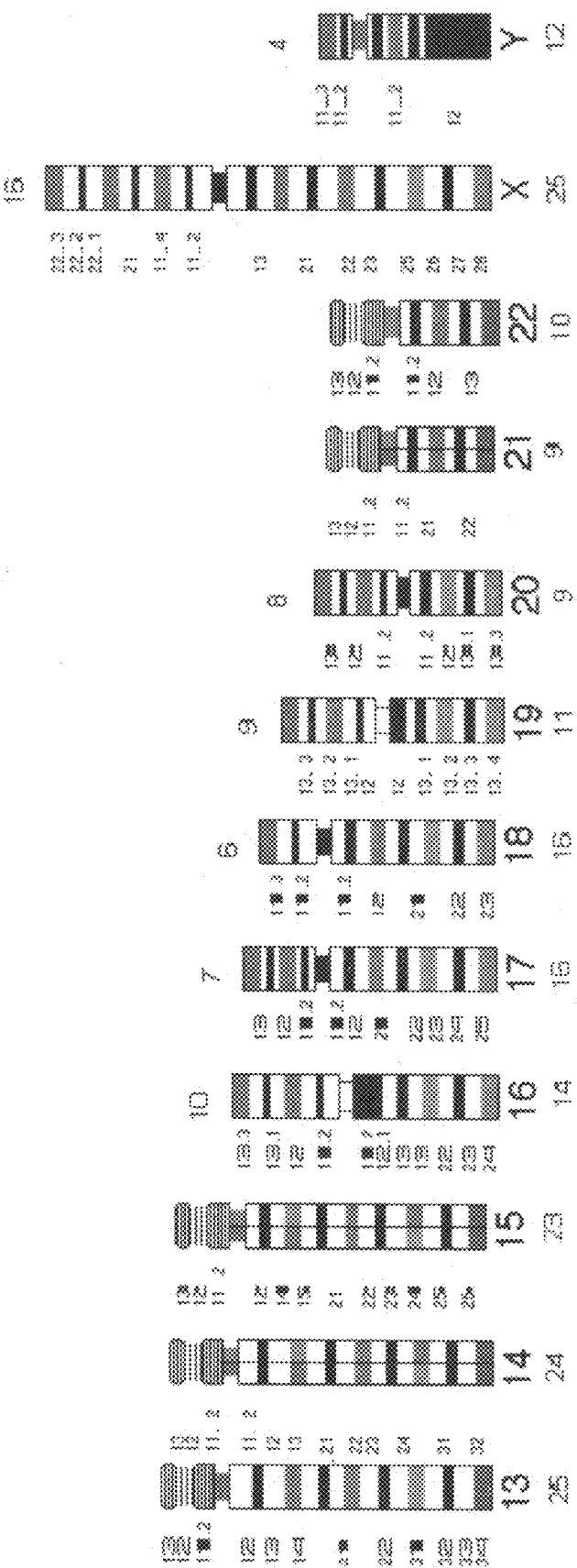
Figure 2A:
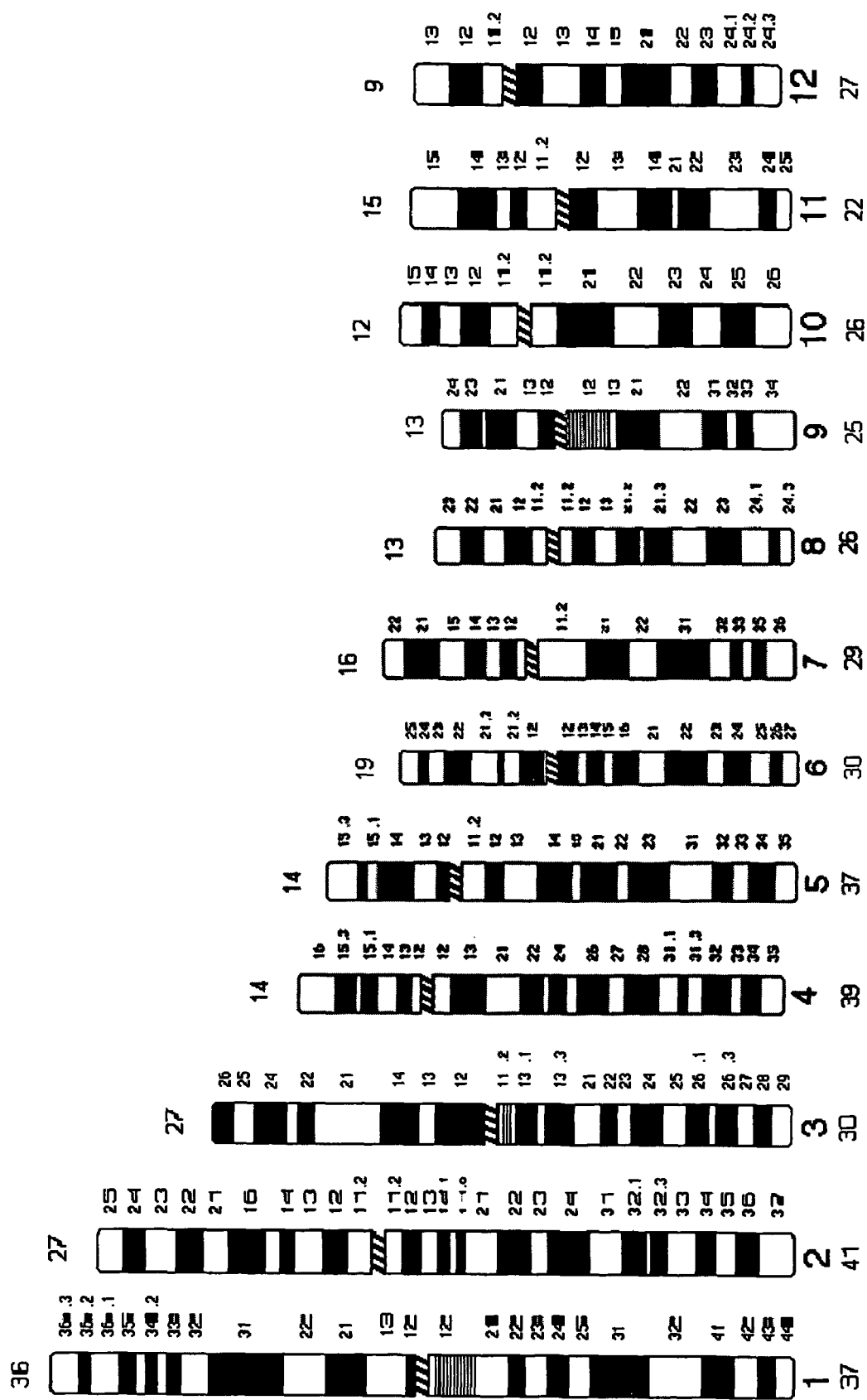
FIGS. 2a and 2b are prior art G-Banding ideograms at the 400 band level.
Figure 2B:
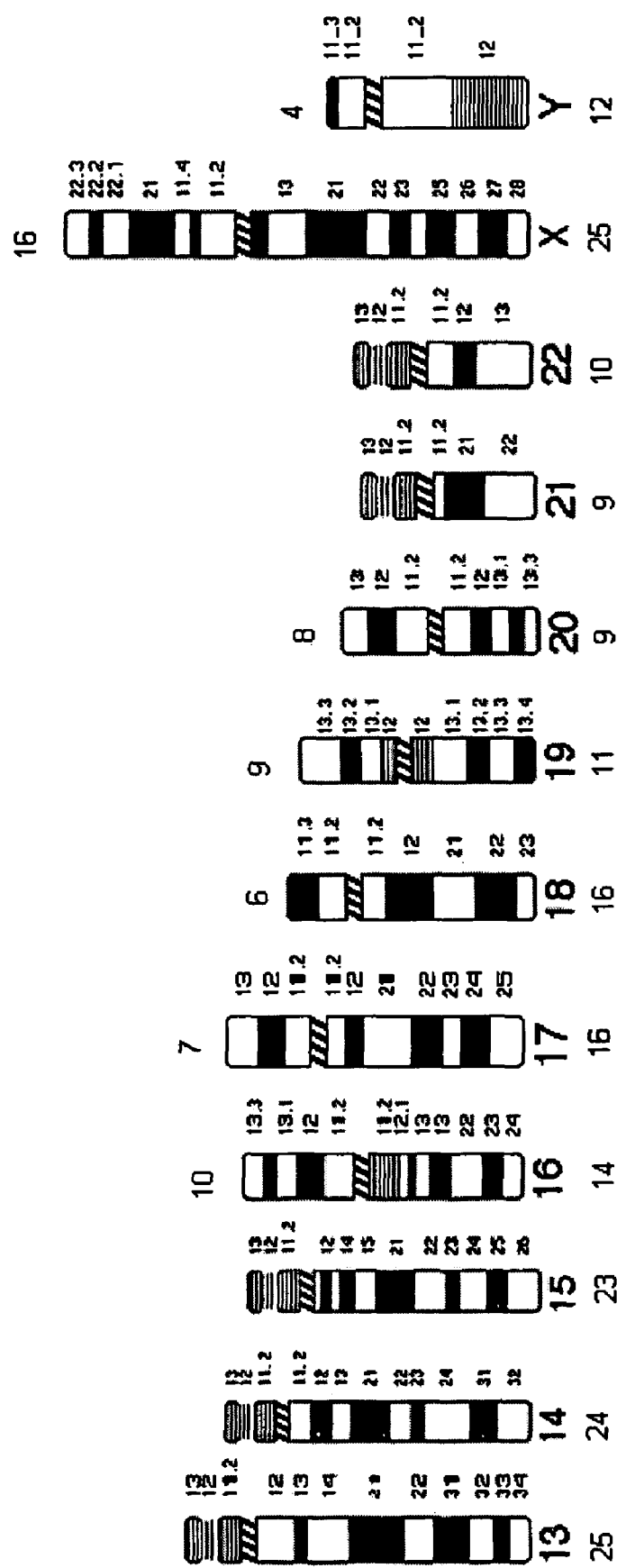
Figure 3A:
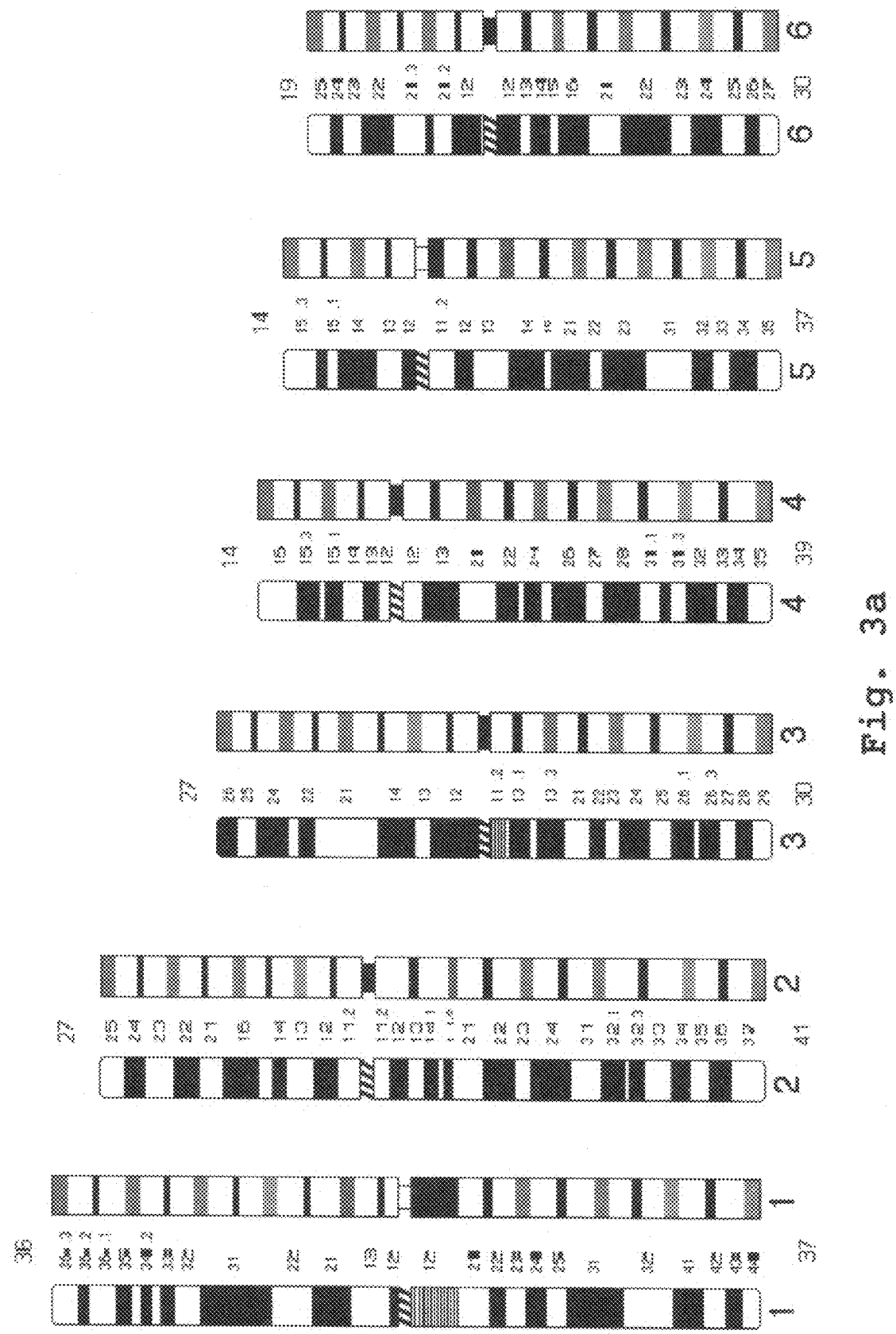
FIGS. 3a through 3d are side-by-side comparisons of Interphase Chromosome Profile (ICP) and G-Banding ideograms according to aspects of the present invention.
Figure 3B:
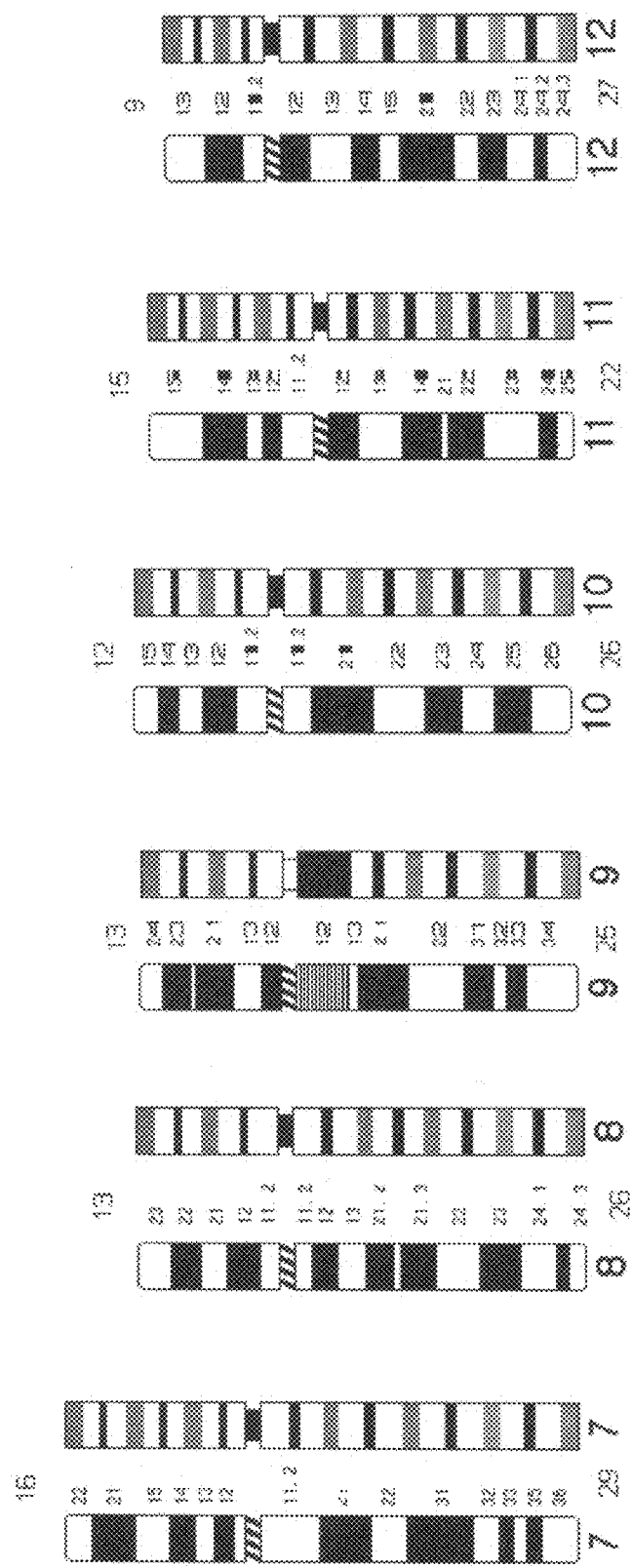
Figure 3C:
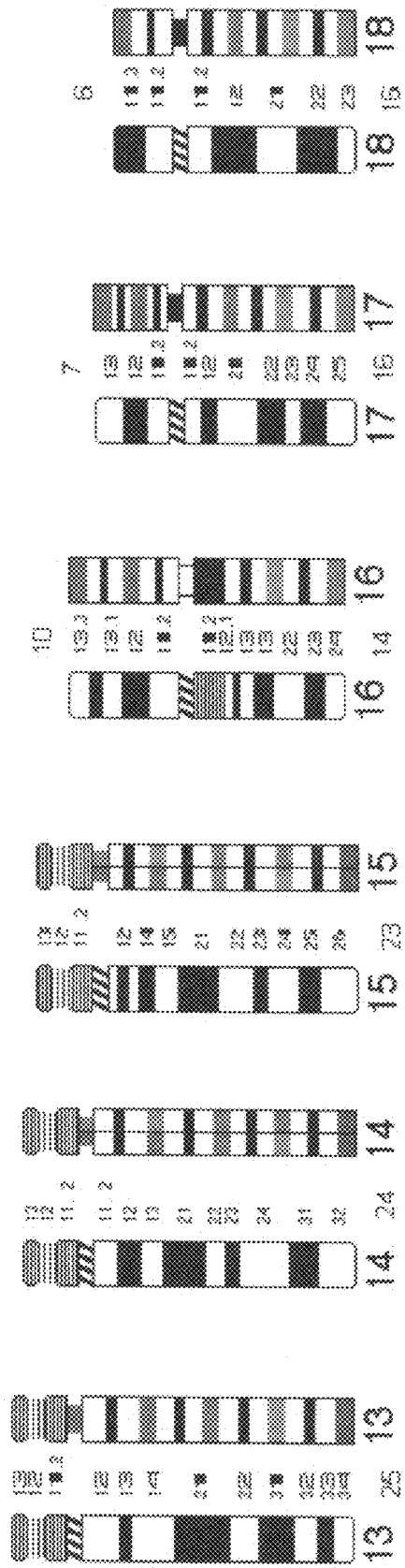
Figure 3D:
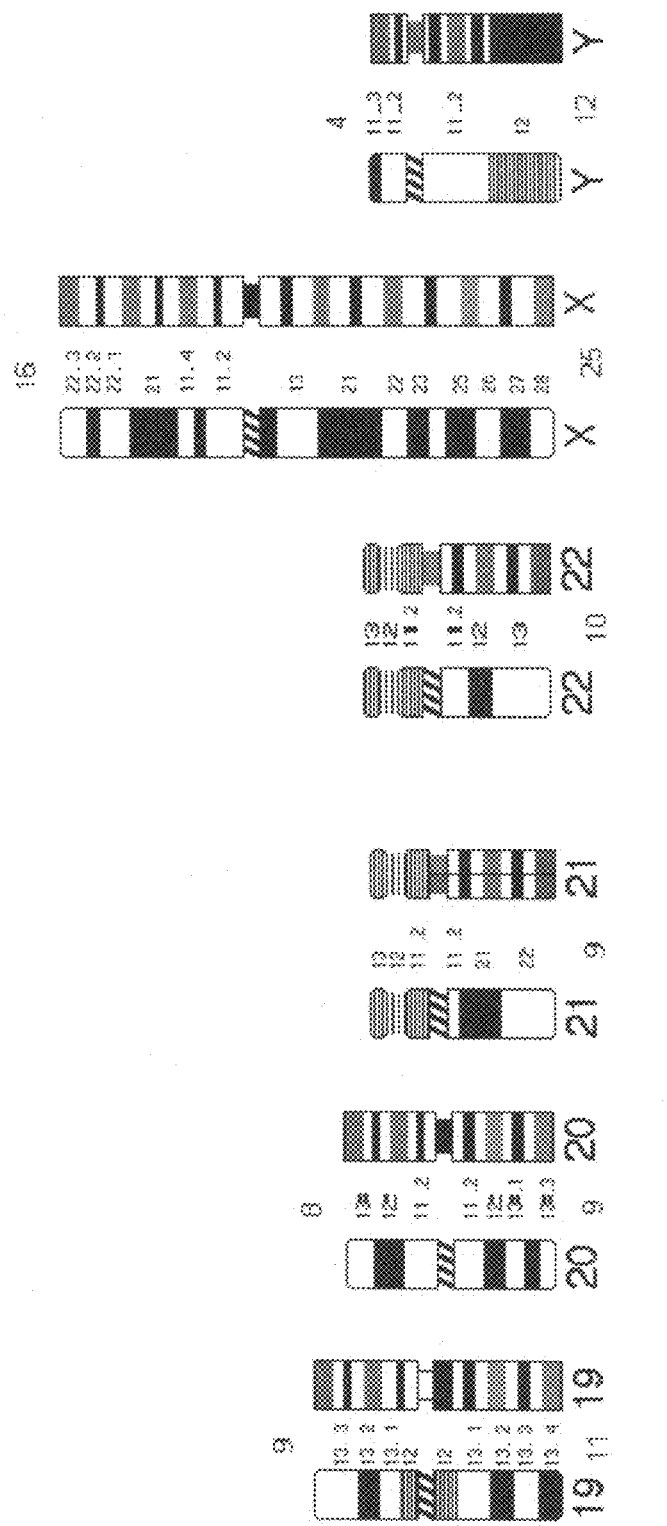
Figure 4B:
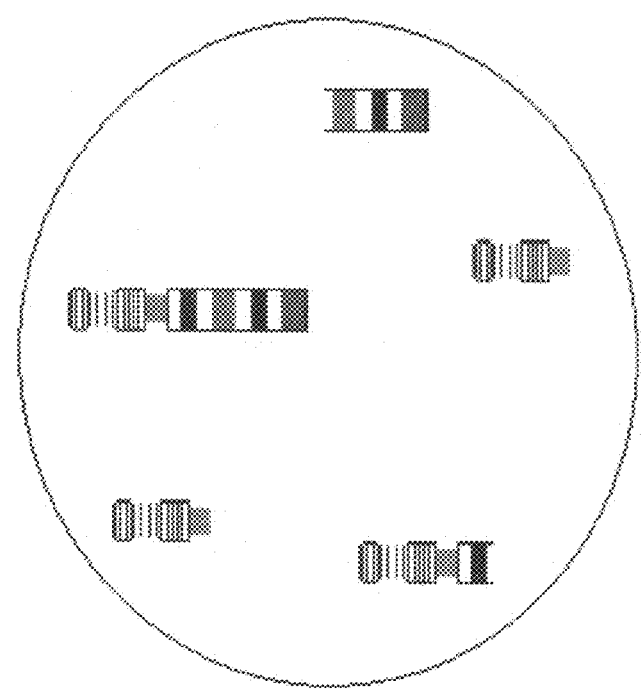
FIGS. 4a and 4b are illustrations of microscope fields showing a translocation between chromosomes 9 and 22, respectively, according to aspects of the present invention.
Figure 4A:
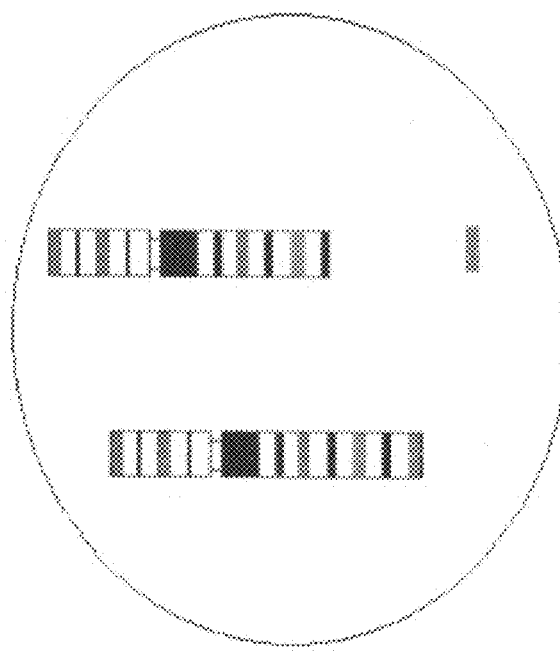
Figure 5B:
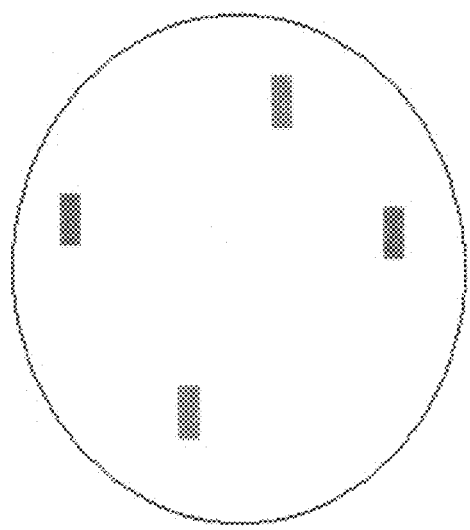
FIGS. 5a and 5b are illustrations of microscope fields showing a translocation and no translocation, respectively, for verification purposes according to aspects of the present invention.
Figure 5A:
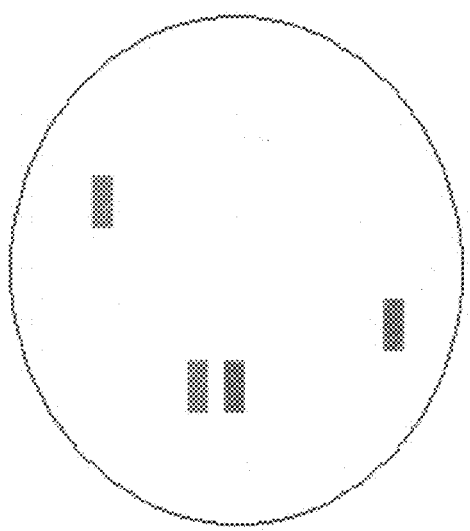

Referring now to FIG. 1, each chromosome is represented by the ICP color band ideogram. Centromere/Pericentromere areas are in Black; short arm telomeres in Blue; and long arm telomeres in Red. For acrocentric chromosomes 14, 15 and 21, the ICP ideograms are split into two parts: Left and Right. The left ideogram represents the color banding when the chromosome was introduced first and the right ideogram represents the color banding when the chromosome was introduced second. The terms first and second refer to the order of the respective chromosome in the Acrocentric Chromosome Combination on Slide 1. For chromosomes 13 and 22, only one ICP color banding exists, since they are always introduced first and second, respectively. FIG. 2 represents the traditional G-banded ideogram at 400 band level.

Each chromosome, such as, for example, a human chromosome can be identified in the Interphase by virtue of the hybridization of specific DNA sequences on the various chromosomes. These sequences can be located on the chromosome's centromere or telomere, or region-specific areas that lie between the centromere and telomere. The spacing of the sequences on the chromosome is designed to be substantially equidistant based on the overall size of the short arm and long arm of the chromosome. Using the substantially equidistant concept, all human chromosome arms can be classified into one of three groups: Group 1 (small), Group 2 (medium), and Group 3 (large). Within each group, individual bands are spaced substantially the same distance apart. This spacing coupled with the disclosed staining technique produces a unique color-banding pattern for each chromosome. The chromosomes are classified into several groups based on their size, and chromosomes within each group have the same color sequence pattern for ease of recognition.

Each chromosome arm can have a distinct color band "signature." Any variations from this signature can indicate a genetic change (i.e., a chromosomal abnormality). In general, the centromere of the chromosome is stained black, and as one proceeds from the centromere towards the end of the arm, the color bands are produced by an admixture of varying proportions of the two primary colors used to highlight the chromosome end (telomere) bands. By way of example, if the short arm telomere is stained blue, and the long arm telomere is stained red, the color band between the centromere and a telomere can be varying degrees of mixtures of red and blue, such as dark red, dark blue, light blue, violet and reddish brown. With this color differentiation, chromosomal variations can be easily recognizable in the Interphase cell under a simple light microscope, without any manipulation of colors by methods currently used in the art for FISH-based detector, filters, dichroic mirrors, CCD cameras, sophisticated computer software, or interferometric spectroscopy.

In an alternative embodiment, the chromosome can be stained black or other differentiating color at additional equidistant locations along the short and long arms of the chromosome between the differential color staining locations. Such additional staining allows for easier visual detection of genetic abnormalities by increasing the resolution as well as providing landmarks for the user to identify. As used herein the color differentiating bands are referred to as Major bands and the additional solid bands, such as, for example, the black bands are referred to as the minor bands.

To provide further differentiation between the short arm and the long arm of the chromosomes, the short arm and long arm minor bands can be stained to provide differing band thicknesses between the respective chromosome arms. For example, the short arm minor bands can be stained to provide minor bands having a uniform thickness smaller than the minor bands on the long arm of the chromosome. Such staining can provide easier detection of an abnormality involving a single chromosome.

Unlike FISH, the current invention relies upon Colorimetric In Situ Hybridization (CISH) for the detection of the hybridized sequences. According to aspects of the present invention, an admixture of specific enzymes conjugated to the DNA probes in specific proportions can result in the production of various colors. This can allow for the sequential or simultaneous enzymatic reactions at the same site of a chromosome in an Interphase cell.

Currently, the FISH-based approaches in the art utilize specific DNA probes to detect known genetic abnormalities either using metaphase chromosomes or Interphase nuclei. In order to establish a diagnosis, one would start with a specific set of probes and if certain results are positive, the test is finished. However, very often the initial "working diagnosis" from the clinician is wrong and the laboratorian is forced to use multiple, sequential applications of DNA probe sets. This is not only very time consuming, but also very expensive. Most unfortunately, there may be an insufficient quantity of testing material (i.e., metaphase or Interphase chromosomes) available to proceed with the sequential hybridizations necessary to complete the karyotype and provide the appropriate diagnosis.

Classical cytogenetic analysis remain the standard because 1) it requires no prior knowledge of the disease; 2) it is capable of detecting not only known, but also unknown genetic abnormalities; and 3) it yields the complete karyotype in one experiment. However, this method requires culture, resulting in significant turn around time. Moreover, for tissue types, such as solid tumors and products of conception, culture success rates are very low, thereby, resulting in little or no relevant information. In addition, marker chromosome identification is often very difficult and impossible with standard G-banding. The present invention overcomes these challenges by not requiring any cell culture and providing a reliable detection mechanism for all types of chromosomal changes in Interphase nuclei, in less than 48 hours.

ICP facilitates the characterization of nearly all chromosome abnormalities through the use of a single universal probe set with no known prior knowledge of specific genetic abnormalities in a specimen. This characterization can occur one chromosome at a time, in the Interphase cells, in a designated spot or well on a hybridization chamber (slide). By way of example, the hybridization chambers comprise a set of three slides, each containing 10 wells. Slide 1 can be used for detecting Robertsonian translocations (translocations between the acrocentric chromosomes (i.e., chromosomes 13, 14, 15, 21, and 22)). Slide 2 can be used to characterize chromosomes 1-10. Slide 3 can be used to characterize chromosomes 11, 12, 16-20, X and Y. In one aspect of the invention, two wells can be left intentionally blank for further testing. The ICP technique can eliminate unnecessary hybridization with numerous different probe sets thereby allowing complete karyotype information to be assembled by combining the results from the 28 wells.

In one aspect of the invention, the ICP technique proceeds according to the following steps: 1) generation of DNA probes; 2) in situ hybridization; 3) colorimetric detection of DNA hybridization; and 4) microscope analysis. Step 1 can comprise using DNA probes from the 24 human chromosomes labeled with a label such as DNP, Biotin, Flourescein and the like. The probes can be specifically generated through chromosomal micro dissection, or other method known in the art, to obtain the exact portion of the chromosome for which hybridization is desired. For example, probe generation can be performed utilizing micro dissection techniques, plasmids, cosmids, computational methods from genome information, synthesis and the like. In Step 2, Interphase cells in each well can be hybridized overnight with a single set of DNA probes specific for the chromosome or abnormality to be detected. Hybridization can be performed using standard in situ hybridization techniques, such as pretreatment with enzymes to allow DNA probes to penetrate the nuclear membrane and DNA denaturation to separate the two DNA strands. In Step 3, each particular label can be detected through standard detection techniques. The detection can be sequential or simultaneous. Based on the predetermined proportion of colors at different bands along the length of the individual chromosomes, the admixture of two colors for example, two enzyme reactions, generates a new detectable color. The various colors for the bands on the chromosomes can be predetermined and as shown in FIG. 1 can be represented on an ideogram for ease of comparative analysis. According to Step 4, the color development on individual chromosome bands can be observed and understood by a human using a simple, standard light microscope.

In prenatal diagnosis TAT is extremely critical and there can be a significant amount of anxiety experienced by expecting parents associated with the testing. For decision making and pregnancy management, the deadline for obtaining results is within 24 weeks of gestation. In normal circumstances, the standard chromosome test is performed at around 16-20 weeks of gestation with results being available after 10-14 days. Therefore, late gestation amniocentesis testing is generally undesirable. In some clinical situations, it is desirable to perform chromosome testing within the last few weeks of pregnancy. Under circumstances, the results need to be obtained on an emergent basis. In early amniocentesis testing (i.e., 12 weeks), results will usually take significantly longer than 10-14 days. This is usually due to the small number of cells available for testing. In each of these situations, the classical cytogenetics cannot generally identify the nature of marker chromosomes. As a result, special studies need to be performed which involve additional time and money. Traditional FISH testing can be done within 48 hours, but, it is highly limited in scope and cannot produce complete chromosome information that includes the detection of any Robertsonian translocations which can potentially increase morbidity through conditions, such as, Uniparental Disomy (UPD).

Peripheral blood chromosome testing can be performed on patients with abnormal phenotypic features, such as, for example, mental retardation or couples with infertility issues or multiple miscarriage, to establish genetic diagnosis. In general, using current methodologies, the TAT for such testing is usually 5 days, however, the regular chromosomal study cannot identify marker chromosomes and unbalanced chromosome rearrangements. These situations require additional testing which increases the TAT and adds to the cost. In certain conditions, abnormalities involve the ends of the chromosomes (i.e., subtle rearrangements), that can be missed with routine testing. Currently the detection of these abnormalities requires expensive FISH testing to resolve whatever diagnostic issues may exist.

For example, in patients with conditions such as, idiopathic mental retardation (ID), approximately 5-9% will have sub-microscopic, sub-telomere rearrangements that cannot be detected by classical cytogenetics. Moreover, in approximately 7% of all patients with normal karyotypes having ID, developmental disorders, will have sub-telomere rearrangements. In some cases additional cells need to be analyzed by routine testing which can significantly increase the cost.

In Leukemia/Lymphoma cancer testing, chromosome information is not only vital in accurate diagnosis, but also critical in managing different drug regimen protocols. Often a physician can be waiting for results to make critical treatment decisions. With current methodologies, TAT is usually about 5 days. One major drawback to current testing is that the regular chromosome study cannot identify marker and derivative chromosomes as well as the previously mentioned subtle rearrangements that involve the telomeres of the chromosomes. These situations can require additional testing resulting in increased TAT and cost. In some cases with normal/abnormal results, many more cells need to be analyzed by routine testing which can also increase the cost. Unfortunately, in many cases, additional cells with chromosomes are simply unavailable for testing. In approximately 5-10% of cases, no chromosome results are available at all, due to culture failure.

The importance of chromosome information in solid tumor diagnosis and patient management is increasing rapidly. In cancers of solid tissues such as bladder, prostate, kidney, breast, lung and the like a regular chromosome study can take up to 30 days or more and in more than 70-80% of the tests, the results cannot be obtained. This results in a high incident of study failure. Similar to the leukemias and lymphomas discussed above, marker and derivative chromosome identification is not possible with regular chromosome testing.

Chromosome information can be obtained on miscarriage material to establish genetic diagnosis and to counsel the patient for future pregnancy decisions. Using current methodologies, the TAT for genetic testing on such tissue can be up to 30-45 days. More importantly, in 20-40% of cases, results cannot be obtained by standard chromosome testing due to a compromised sample. Accordingly, additional testing is generally required to properly diagnose the genetic abnormality and counsel the patient. Such additional testing subsequently increases the costs and time required.

ICP fills the void created by the limitations of current methodologies by providing the unmet needs of the clinical cytogenetics and medical community, in a timely and cost effective manner.

Following are examples illustrating procedures for practicing the invention. These examples should be construed to include obvious variations and not limiting.

Example 1

Use of the Hybridization Chambers

Under current methodologies 24 different colors are used to obtain a multi-color karyotype, based on metaphase chromosomes. To produce metaphase chromosomes, the material from various specimen types, such as for example, peripheral blood, bone marrow, amniotic fluid, solid mass and the like must be cultured. It is generally necessary to study 20 cells to obtain complete karyotype information. Often, the amount of cells available is limited. Until the present invention, no method has been available to effectively utilize the source material, so that complete characterization of the genetic changes present in the specimen presented for study, can be accomplished. There are some methods existing in the art capable of studying specific sets of chromosomes; however, these methods are quite limited. As discussed above, suspected genetic abnormality must be known beforehand and only limited information can be gained by such testing. Using the present invention with a single universal probe set, without any prior knowledge of the specific genetic changes present in a specimen, nearly all chromosome changes can be completely characterized. This can be done one chromosome at a time in Interphase cells, in a designated spot or well on a hybridization chamber.

In one aspect of the invention, a hybridization chamber can consist of a set of slides and as illustrated in the diagram, each slide can contain wells. By way of example, Slide 1 can be a slide for detecting a special type of chromosome rearrangement called Robertsonian translocation. Robertsonian transolocations are translocation between acrocentric chromosomes that join by their centromeres, resulting in one less centromere in the karyotype. For example, when a Robertsonian translocation takes place between chromosome 14 and chromosome 21, in a balanced form, there is one normal 21, one normal 14 and a joined chromosome 14/21 in the karyotype, so that the total number of chromosomes changes from 46 to 45. There are five acrocentric chromosomes in a human genome (chromosomes 13, 14, 15, 21 and 22), any one of these five can participate in this type of rearrangement, including rearrangement between both copies of the same chromosome, i.e., chromosome resulting in 21/21 joined chromosome. The rearrangement can result in a balanced or unbalanced karyotype. In an unbalanced form, the total chromosome number generally remains 46, however, there will likely be three copies of one of the acrocentric chromosomes in the karyotype.

Using current FISH methods, on a clinical sample from a patient having Down syndrome, three copies of Down syndrome specific region i.e., 21 q22, will generally be detected. Such a result is sufficient for the free form of Down syndrome having three copies of chromosome, 21, and without the presence of Robertsonian translocation. However, the same clinical phenotype of Down syndrome can result from the Robertsonian rearrangement involving chromosome 21 and one other acrocentric chromosome. This cannot be detected using the current methods in the art. This has important clinical implications for genetic counseling and next pregnancy management as recurrence risk figures are entirely different between the free form and the Robertsonian form of Down syndrome. Accordingly, valuable information is lost. This limitation can be overcome by the current invention.

Robertsonian translocation involving chromosomes other than chromosome 21 can also be clinically significant in prenatal diagnosis. A pathological condition called Uniparental Disomy (UPD) exists for chromosomes 13, 14, and 15. When balanced Robertsonian translocations occur between acrocentric chromosomes, and the chromosome involved is 13, 14 or 15, the carriers have an increased risk for UPD. UPD in the fetus, detected in the prenatal diagnosis, contributes to severe clinical manifestations and adds significantly to the rate of morbidity. Until the current invention, the only way to detect the Robertsonian translocations and recognize potential UPD, was by standard cytogenetics. ICP overcomes this by detecting all Robertsonian translocations in Interphase cells, thus providing valuable information for the pregnancy management, in the prenatal diagnosis.

Slide 2 can comprise wells for chromosomes 1-10. Slide 3 can comprise wells for chromosomes 11, 12, 16, 17, 18, 19, 20, X/Y with additional wells left intentionally blank for further testing. By carefully plating 25-30 Interphase cells in each well, even compromised specimens can be studied because unnecessary hybridization is eliminated and complete karyotype information can be assembled by combining the results from the wells.

Example 2

DNA Probe Set

The probe set consists of a uniquely designed combination of DNA probes for each of the 24 chromosomes. Each human chromosome contains a centromere and one short arm and one long arm attached at the centromere. All chromosomes contain at the ends of the arms, specific DNA sequences called telomeres unique for each chromosome. Acrocentric chromosomes only have centromeres and long arms. Their short arms are variable and can be absent in the genome and have no clinical significance. For this reason no probes are designed to detect the acrocentric short arms.

Referring now to FIG. 1, illustrating the color banding pattern based on the present invention. For comparison, the standard G-banding (i.e., the gold standard), is included. The ideogram is the diagrammatic representation of all the bands on a chromosome. Based on the current G-banding ideograms, each human chromosome was given a individual unit length. For example, chromosome 1, the largest human chromosome, has a unit size of 73, with short arm having a unit size of 36 and the long arm 37; chromosome 2 has unit size of 68 with 27 and 41 for the short and long arms, respectively. The unit sizes for all chromosomes are depicted on the ideograms.

Under current methodologies, the chromosome classification is generally based on G-banding patterns and chromosomes are grouped A through G and by sex chromosomes. Chromosomes 1-3 are in group A, 3-4 in B, 6-12 and X are in C, 13-15 in D, 16-18 in F, and 19-20 including the Y chromosome are in G. The bands on individual chromosomes are generally produced by chemical staining and have fixed locations on the chromosome and cannot be changed. Therefore, identification of chromosome changes that fall between two naturally, closely spaced G-bands can be, and is often, very difficult. This problem can be overcome by the present invention by spacing the "bands" at substantially equidistant locations from one another based on the overall size of the short and long arms. This can allow for the easy recognition of chromosomal changes in Interphase nuclei.

Utilizing the concept of substantially equidistant chromosomal hybridization, human chromosome arms can be classified into one of three groups: Group 1 (Small) having a unit size of 4-6; Group 2 (Medium) having a unit size of 7-19; Group 3 (large) having a unit size of 20-41. With in each group, individual bands are spaced at substantially the same distance. By way of example, the short arm can have 5 bands and the long arm can also have 5 bands. With the centromere band, chromosome 1 has a grand total of 11 (5+1+5) color bands. Accordingly, looking at human chromosome 1 in an Interphase cell, using the current ICP invention, one would observe, starting from the end of the short arm, a color band, a "non-color" band, a color band, a non-color band etc. until they reach the centromere and this pattern would continue until they reach the end of the long arm with a color band. Counting all bands, color and non-color, a normal chromosome 1 would have a grand total of 21 bands. This type of resolution is equal or better than the standard G-banding pattern, which requires metaphase chromosomes, which can only be obtained after culture. By way of another example, following the above model, chromosome 18 would have a group 1 short arm and group 2 long arm; chromosome Y would have a group 1 short arm and a group 1 long arm.

As a further example, with respect to chromosome 1, minor bands can be stained interstitially at locations between the color bands. Such minor band staining, for example, can add eight (8) additional bands, bringing the total stained bands on the chromosome to nineteen (19).

As can be seen in FIG. 1, the classification method is illustrated with the corresponding color banding pattern for human chromosomes. In general and for illustrative purposes only, centromere bands can be stained black and as one proceeds from the centromere towards the end of the short arm, the color bands can be produced by an admixture of varying proportions of two primary colors used to highlight the chromosome end (teleomere) bands. In one aspect of the invention, short arm telomere bands can be stained blue and long arm telomere bands can be stained red. In another aspect of the invention, for chromosomes 1, 5, 9, 16 and 19 the pericenromeric band, i.e., the band adjacent to the centromere, can be used in lieu of the centromere.

For illustrative purposes only, using chromosome 1 as an example, the centromere can be black, the next band in the short arm can be 1blue:9red yielding a dark red color. The next band can be 7blue:3red yielding a light blue color. The next band can be 5blue:5red yielding a violet color. The next band can be 3blue:7red yielding a reddish brown color. Finally, the telomere band can be 100% blue indicating the end of the telomere. This sequence of bands, between centromere and temolere, of 3:7, 5:5, 7:3 can be reversed with respect to the primary colors for the long arm. Therefore, the long arm of chromosome 1 starting with centromere black, will have 3red:7blue (reddish brown); 5red:5blue (violet); 7red:3blue (light blue) and finally the telomere band red (100%). A simple read out of whole chromosome from short arm to long arm is blue, reddish brown, violet, light blue, dark red, black, reddish brown, violet, light blue and red. As can be seen from this discussion each arm has its distinct color band "signature" and any variations from this signature would indicate a genetic change.

According to aspects of the present invention, variations can be easily recognizable in the Interphase cell, under a simple light microscope without the need for the manipulation of colors by filters, dichroic mirrors, CCD cameras, sophisticated computer software; inferometers and the like, as are currently used in the art for FISH based detection of chromosome changes. Because the color bands according to the present invention are spaced more or less equidistant from each other, regardless of the size of the arm, deviations from the color sequence, missing or extra color bands, reduction or enlargement of unit size of non-color bands, displacement of the color sequence would indicate chromosomal abnormalities. This method can be used for detecting both numerical and structural abnormalities of virtually any human chromosome. A few examples of chromosome abnormalities and especially marker chromosome identification using ICP are discussed infra. Under current methodologies, marker chromosomes could only be identified in metaphase chromosomes. Utilizing the present invention, marker chromosomes can be identified in Interphase nuclei. The result is a significant savings of time and money.

Example 3

The CISH Method

The present invention utilizes colorimetric in situ hybridization (CISH). There are numerous advantages to using CISH. The most significant advantages are the practicality of the available equipment in the cytogenetics laboratories and the avoidance of the extraordinary cost associated with FISH based equipment. While the FISH based approach is sufficient in a research environment, CISH is uniquely situated for routine clinical cytogenetics and other pathology laboratories. As discussed above, chromosomal abnormalities are readily recognizable in the Interphase cell, under a simple light microscope without manipulation. Utilizing the CISH method, there are no pseudo-color representations as in the multi color FISH methods. In addition, generally what is seen under the scope is what the test yields; a true color representation. The color described above, for example, is designed for an ordinary, "non-color blind" human eye that can discriminate the adjoining colors. This opens additional opportunities for current cytogenetic analysis for even those not as highly skilled in the field, such as technicians. Therefore, there is an opportunity for significant financial and time savings, as highly skilled technologists are both expensive and difficult to find Current CISH methodologies utilize only whole enzymatic reactions to produce specific colors at the site of reaction. Admixtures of specific enzymes conjugated to DNA probes, in specific proportions as described herein, to produce differing colors has not been disclosed. While sequential enzymatic reactions at different sites with in an Interphase nucleus have been known to those in the art, until the present invention, sequential enzymatic reactions at the same site (i.e, any given site, in the Interphase nucleus) has not been possible. A major disadvantage of CISH as compared to FISH was the resolution (i.e., the brightness) of the signal, at the site of the reaction. In the past few years several advances have been made in the field of CISH, so that amplification of the signal, at the site of the reaction is now possible, if desired. In addition, with the incorporation of multiple ligands, to which the enzymes are later attached, during the DNA probe preparation steps, the signal intensity for the color bands can be enhanced.

The CISH method has the advantage of being permanent. The color reaction produced is permanent and can be preserved for later use. On the other hand, FISH signals fade rapidly and are not at all useful for retrospective analysis. As new genetic changes are discovered in a patient (i.e., during treatment), in order to establish clinical correlations, having a previously hybridized slide will be extremely useful to use for comparison purposes.

Example 4

Working Example

Current cytogenetic methodologies rely on natural breakpoints in a chromosome for designing probes that flank these regions. For example, to detect a leukemia specific translocation such as the translocation between chromosome 9 and 22, probes are designed to detect the breakpoint on chromosome 9 in band 9q34 (the abl gene) and band 22q11.2 (the bcr gene). Using two colors, red for 22 and green for 9, a normal Interphase reaction appears as two red dots and two green' dots, whereas a translocation would result in one green, one red and one yellow due to the green/red fusion. By way of example, utilizing the present invention, the same translocation would appear as a displacement of chromosome 9 into two segments and chromosome 22 into two segments. The resulting color banding pattern in the chromosome 9 well on the respective slide would be: starting from short arm telomere blue, reddish brown, black, violet, light blue as one contiguous stretch and red away from this stretch i.e., displacement of red which indicates a break between light blue and red, where the abl gene on chromosome 9 resides. The non-separated color sequence in the same well represents the normal chromosome 9. Similarly, the color band pattern on chromosome 22 would be red separated from the violet, dark blue stretch indicating a break between red and violet. The bcr gene on chromosome 22 lies between the two color bands red and violet. Again, the non-separated color pattern of red, violet and dark blue indicates a normal chromosome 22. Since chromosome 22 centromere cross hybridizes with chromosome 14, two additional separate red signals will be present. Chromosome 14 hybridization wells will also have 2 extra red or blue dots. If this were the only genetic change in that specimen, as one proceeds to read the ICP slides, all wells containing chromosome 22 would exhibit the above pattern, the well containing chromosome 9 would have the above color pattern and all other chromosomes will have two stretches of contiguous color band pattern. Depending on the sex of the patient, either XX or XY, chromosome color pattern would be read in the well containing the X and Y chromosome probes. As can be seen from this example, prior knowledge of the disease status is unnecessary for using the ICP method.

In an embodiment according to aspects of the present invention, in a simple translocation like the above example of a 9:22 translocation, confirmation of the translocation can be accomplished by visual means. Each of the individual color bands, including the interstitial black minor bands, in the genome for all human chromosomes can be available in the kit as a red or blue band. As previously indicated, there can be slots or wells left empty intentionally in the hybridization chamber for optional and/or confirmatory tests. Thus, selecting one of the non-centromere or non-telomere bands on either side of the breakpoint on chromosome 9 and chromosome 22 and introducing them into the hybridization chamber, any Interphase cells harboring the translocation would have a color pattern of red, red, blue, blue. The juxtaposition of red and blue would indicate the translocation. Cells not harboring the translocation in this color scheme would have a reading of red, red, blue and blue. Since centromere bands are not introduced, the cross-hybridization for chromosome 22 is therefore eliminated.

By way of example, this color scheme can be used to verify virtually any simple translocation, regardless of the chromosome band involved. Even complex translocations involving more than two chromosomes can be detected and diagnosed by systematic additional hybridizations using the above described method.

Example 5

Marker Chromosome Identification

Marker chromosomes, by definition in clinical cytogenetics, indicate that by standard G-banding technique, the origin of the centromere and the additional material on that chromosome could not be identified. Yet these marker chromosomes play an important role in the disease generation and/or progression. Using metaphase chromosomes and the 24-color FISH techniques, one can generally identify the nature of the marker chromosomes. However, identification in the Interphase nucleus is very challenging and using current methodologies, cannot be performed.

An example of a marker chromosome is described as follows: having the centromere of chromosome 3; all of the short arm of 3; two bands from chromosome 7 long arm; and a long arm telomere from chromosome 10. This is a very complex marker and in cancer cytogenetics, especially solid tumor cytogenetics, one encounters this type of situation routinely.

Figure 6C:
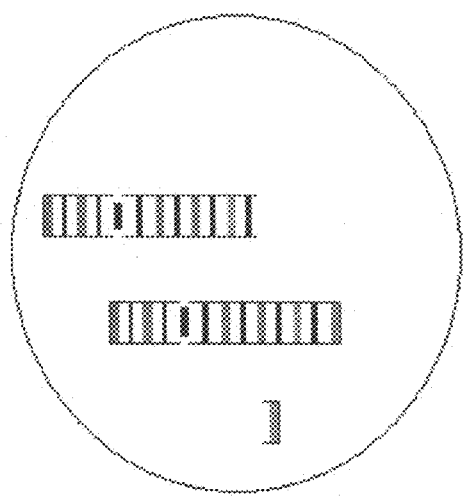
FIGS. 6a, 6b and 6c are illustrations of marker chromosome identification in chromosomes 3, 7 and 10, respectively, according to the aspects of the present invention.
Figure 6B:
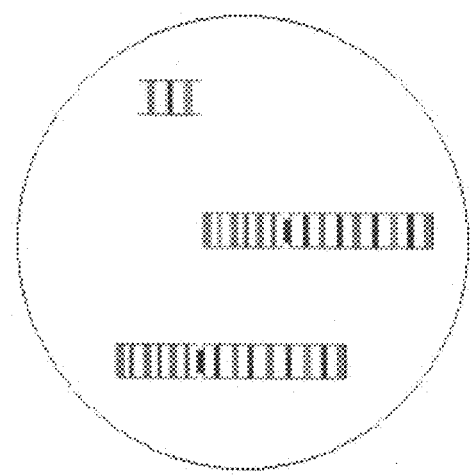
Figure 6A:
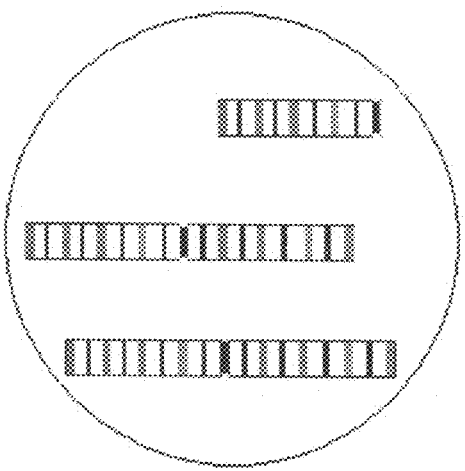

By utilizing the techniques of the present invention as described herein, in the ICP model, hybridization is completed utilizing a three slide technology, the following results will be read: Slide 1 unremarkable (i.e., normal); Slide 2, 1-2, 4-6, 8-9 (i.e., normal); Slide 3 unremarkable (i.e., normal). On Slide 2, in the hybridization well for chromosome 3, an abnormal color band pattern would be read. In addition to the two normal contiguous color bands, an extra centromere and short arm bands will likely be present. Similarly in the chromosome 7 well in addition to the two contiguous color bands, two extra, adjacent color bands will be present. Finally, in the chromosome 10 well, depending on whether chromosome 10 long arm telomere composition is balanced or not, one could observe either two contiguous color bands, and an extra telomere separate band or one contiguous stretch of color bands and the displacement of the telomere band from the second color band sequence. FIG. 6 depicts the marker chromosome in three different Interphase cells.

Figure 7:
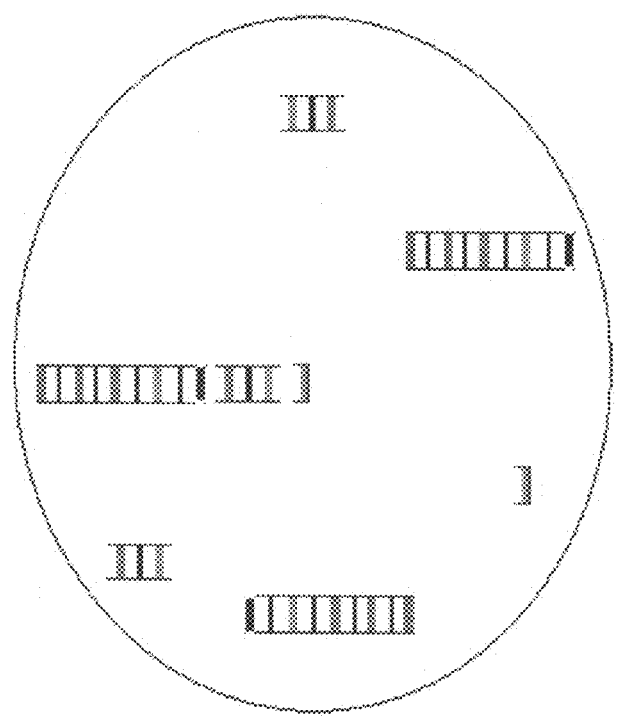
FIG. 7 is an illustration of the resulting microscope field from the marker chromosome identification involving chromosomes 3, 7 and 10 according to aspects of the present invention.
Figure 8:
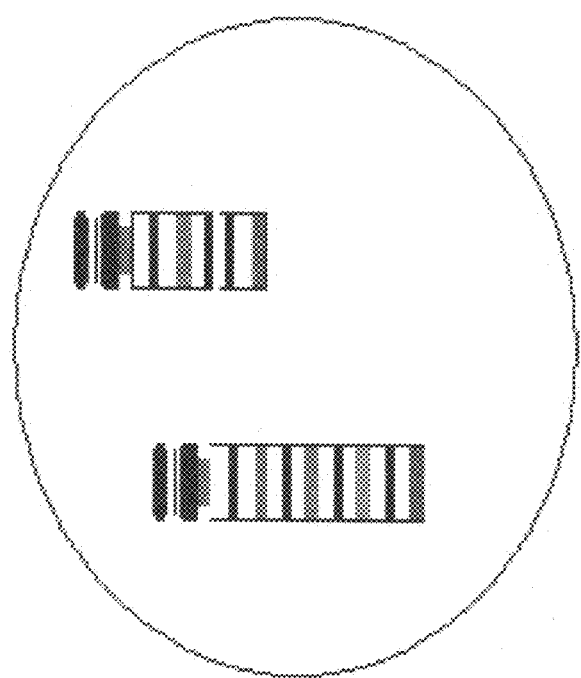
FIG. 8 is an illustration of a microscopic field showing an interstitial deletion of chromosome 13 according to the aspects of the present invention.
Figure 9:
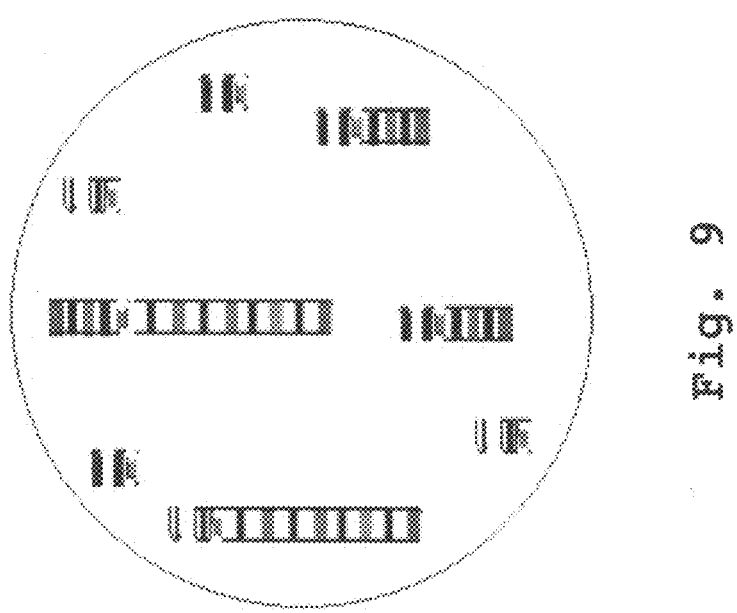
FIG. 9 is an illustration of a microscopic field showing a Robertsonian translocation of chromosomes 14 and 21 according to the aspects of the present invention.
Figure 10:
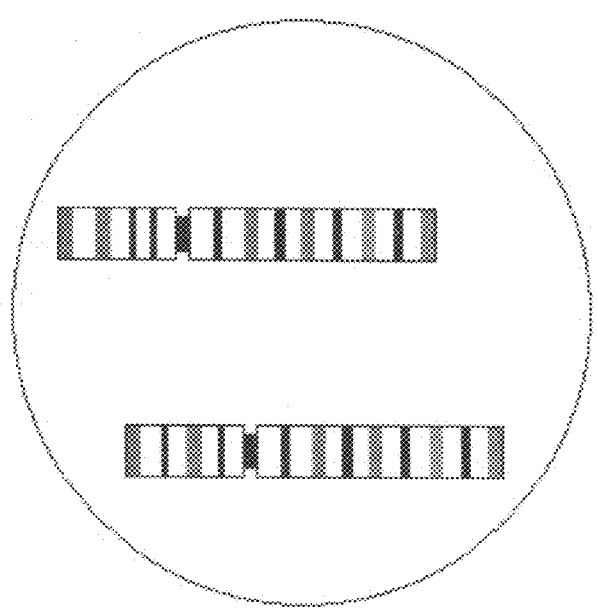
FIG. 10 is an illustration of a microscopic field showing a paracentric inversion of the short arm of chromosome 8 according to aspects of the present invention.
Figure 11:
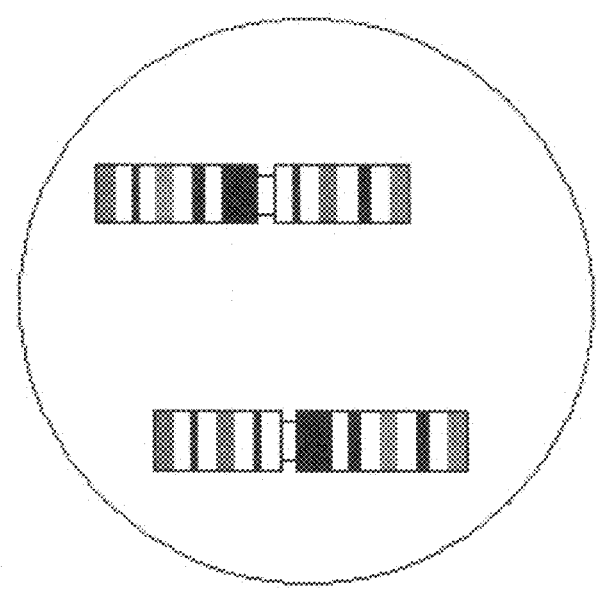
FIG. 11 is an illustration of a microscopic field showing a pericentric inversion of chromosome 16 according to aspects of the present invention.
Figure 12B:
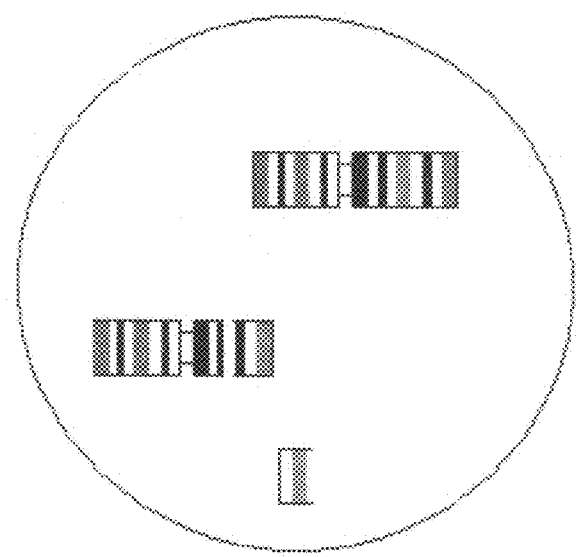
FIGS. 12a and 12b are illustrations of microscopic fields showing insertional translocations involving chromosomes 17 and 19, respectively, according to aspects of the present invention.
Figure 12A:
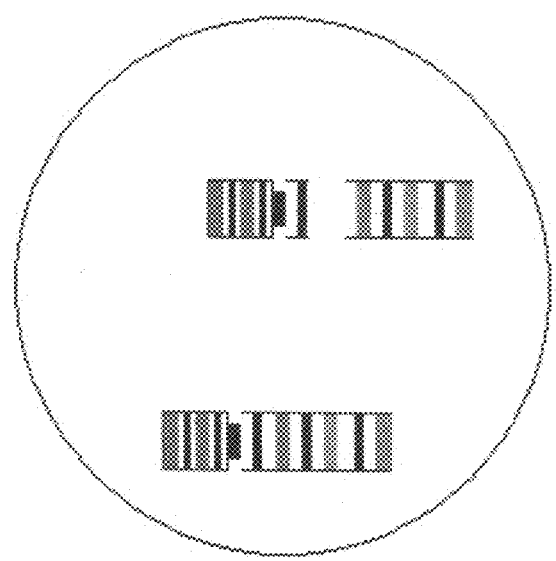
Figure 13B:
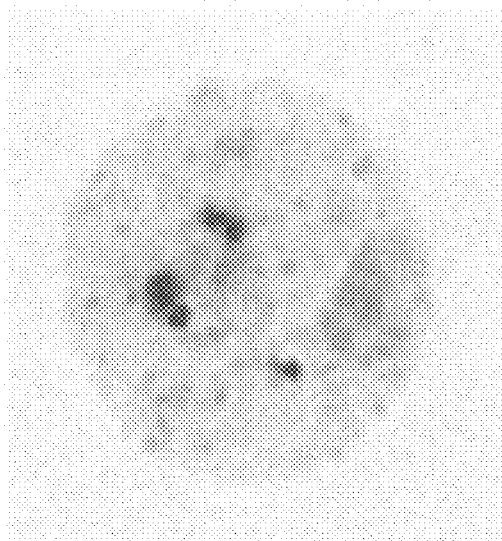
FIGS. 13a and 13b are photomicrographs of prior art colorimetric in situ hybridization.
Figure 13A:
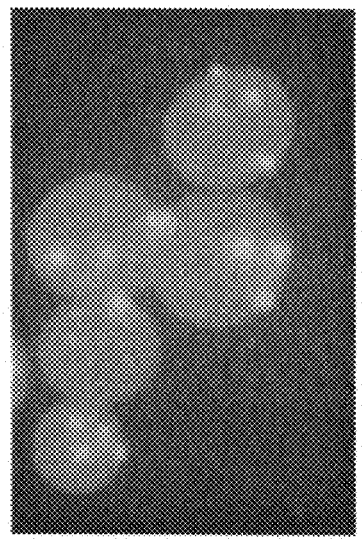

According to aspects of the present invention, in the ICP model, the marker chromosomes can be "reconstructed". Taking the centric fragment from 3, and the acentric fragments from 7 and 10 and hybridizing all together in an Interphase cell, one can confirm whether all of these fragments formed the "suspected" marker. If a contiguous color band sequence was found, the results are likely positive. In addition, the corresponding bands on the normal chromosomes 3, 7 and 10 will also likely highlight, thereby confirming the nature of the marker chromosome. FIG. 7 depicts the "reconstructed marker" with the remaining color bands as discussed herein.

TABLE A

| 1 | 2 | 3 | 4 | 5 |
|---|---|---|---|---|
| 13/14 | 13/15 | 13/21 | 13/22 | 14/15 |
| 14/21 | 14/22 | 15/21 | 15/22 | 21/22 |
| 6 | 7 | 8 | 9 | 10 |

Table A represents the acrocentric chromosome combination on slide 1 according to aspects of the present invention. Depending on whether the chromosome was introduced first or second, the centromere would have a red or blue color with the remaining color sequence as depicted on the ideograms. Color sequence to the left of the chromosome on the ideogram represents first and the sequence on the right represents second in the combination. For chromosomes 13 and 22, only one color is represented because they are always introduced only either first or second.

Since chromosome 13 and 21 centromeres can cross hybridize, in well #3, all centromeres will be violet (red+blue). This holds true regardless of whether there is a translocation between these two chromosomes. When there is a translocation, in the balanced state there will be one less centromere (i.e., 3 in stead of 4) in Interphase cells in this well, whereas, in the unbalanced state, the number remains 4. The same general rule applies to chromosomes 14 and 22 as well. Therefore, Interphase cells in well #7, will act similarly to chromosomes 13 and 21. Both in the balanced and unbalanced state, there will likely be a larger contiguous stretch of colors from both chromosomes absent the centromere, representing the presence of a Robertsonian translocation. In all of the wells except for # 3 and #7, 2 or more extra centromere bands representing the cross hybridization, will likely be present. This design ensures multiple opportunities to cross reference the genetic abnormality.

Example 7

Cell Measurement Technique

According to aspects of the present invention, ICP is amenable to the investigation of all types of specimen types, such as, for example peripheral blood, bone marrow aspirate, amniotic fluid, chorionic villi, pleural effusion, lymph node biopsy, solid tumor mass, products of conception etc. Of these specimen types, only the "liquid" specimens such as blood, bone marrow, amniotic fluid, and pleural effusion contain single cells. The remainder of the specimens are tissues comprising aggregates of cells connected together. In order to perform ICP, one needs single Interphase cells. Thus, according to another aspect of the present invention, a method can be devised to precisely add or plate 25-30 cells in each well on the hybridization chamber slides.

Current methodologies exist to dissociate solid tissues into single cell suspensions, such as those utilizing enzymes like collegenase and trypsin. As discussed supra, liquid specimens generally do not require this type of treatment to obtain single cells. Once a single cell suspension is obtained from any specimen type, the concentration of the cells is adjusted such that each "pipette drop" contains 25-30 cells. For example; if ml of specimen contains 1000 cells and each ml contains 10 pipette drops, each drop then contains 100 cells. Since each well will generally receive only one drop for ICP, the specimen is appropriately diluted, in this case, 3.5-4 times so that each drop can contain the desired cell concentration. If the original volume is 10 cells per pipette drop, then the specimen is concentrated 2.5-3 times by spinning down and removing excess volume, so that each pipette drop can contain the desired cell concentration.

This technique ensures that, even "compromised" specimens, specimens having small volumes, can be analyzed completely under the present invention, whereas other methods in the art might have failed to capture complete karyotype information.

Example 8

Use of Hypotonic Treatment

Most of the FISH methodologies currently only use smears prepared from the specimen with no hypotonic treatment. The discovery of hypotonic treatments such as KCl and Na Citrate solutions, gave birth to the modern cytogenetics field. The proper "swelling" of metaphase cell ensures the separation of metaphase chromosomes when they are dropped onto microscope slides. Similarly, proper separation of Interphase chromosomes is crucial for the successful delineation of a multi-color band sequence. By experimenting with different hypotonic solutions at different concentrations, either singly or in combination, it is likely possible to properly "swell" the Interphase, before it is fixed onto the microscope slide in the hybridization well.

Example 9

ICP Procedure

Generation of Human DNA Probes:
1) On each chromosome, the location of the DNA probe hybridization is depicted on the standard G-banded ideograms. As previously disclosed, Chromosome 1 can have 19 DNA probes: 1 pericentromere, 4 short arm colored+5 short arm black+1 short arm telomere, 3 long arm colored+4 long arm black+1 long arm telomere.

2) Each chromosome band can be, for example, micro dissected or isolated using other techniques known in the art from the standard G-banded metaphase chromosome preparations.

3) Each micro dissected chromosome band can be amplified by DOP-PCR technique as generally described by Telenius (1992).

4) Repeat sequences from these probes can be removed using biotin-labelled Cot-1 DNA, followed by avidin magnetic beads, as generally described by Craig (1997)

5) Repeat-free Probes from the first DOP-PCR cycle can be subjected to further rounds of amplification using the methodology described by Liehr (2002)

6) Using standard sonication techniques, the probe length can be adjusted to between about 200 bp-600 bp. Alternatively, smaller fragments of the probe can be created utilizing standard techniques as a kit, such as Vector labs Nickit kit.

7) The DNA fragments can be labeled with a label, such as, for example, DNP, Biotin, Flourescein or the like, by using standard labeling techniques or technology, such as, Vector Labs FastTag.

8) The label is selected according to a predetermined methodology.

9) The FastTag technology for example, can incorporate the labels at multiple sites throughout the DNA strand to achieve a higher sensitivity at the site of hybridization.

10) DNA probes from the 24 human chromosomes are then ready for in situ hybridization to the Interphase cells on the hybridization chamber slides.

11) Centromere and telomere DNA probes can be created or commercially available probes can be utilized. The probes can be obtained for the ICP purpose without the need for a label and as described above, the appropriate label can be incorporated into the DNA.

In situ hybridization:

1) The single cell suspension can be plated onto each well on three hybridization chamber slides. The suspension is treated with hypotonic solution and fixed with a 3:1 methanol: acetic acid solution.

2) Interphase cells in each well can be hybridized with a single set of DNA probes specific for that well, using standard in situ hybridization techniques, such as, with the pretreatment of enzymes to allow the DNA probes to penetrate the nuclear membrane, wherein DNA denaturation is performed to separate the DNA strands.

3) Hybridization can occur overnight.

4) Post hybridization washes can be done to remove excess, unhybridized probes from the slides.

Colorimetric Detection of DNA Hybridization (CISH)

1) The label biotin can be detected by avidin-D conjugated Glucose Oxidase enzyme, after reaction with a TNBT substrate specific for Glucose Oxidase. This can produce a Black precipitate at the site of DNA hybridization (i.e., at the centromere and pericenromere bands as well as interstitial locations on the short and long arms on all chromosomes).

2) Label fluorescein can be detected by anti-Fluorescein anti-body-conjugated Peroxidase enzyme after reaction with a substrate such as, for example, NovaRed, specific for Peroxidase. This produces a red precipitate at the site of DNA hybridization i.e., at the long arm telomeres and other bands through out the chromosome, on all chromosomes.

3) Label DNP can be detected by anti-DNP anti-body-conjugated Alkaline Phosphatase enzyme upon reaction with a substrate, such as, for example vector blue, specific for Alkaline Phosphatase. This produces a blue precipitate at the site of DNA hybridization i.e., at the short arm telomeres and other bands through out the chromosome, on all chromosomes.

4) The three reactions are carried out in a sequential manner with necessary blocking and washing steps in between. Commercially available substrates use should follow the protocol of the vendor.

5) The sequence can be as follows: Biotin, Fluorescein, and DNP detection.

6) In the alternative, it is possible to complete all three reactions simultaneously, because the enzymes are different and the substrates are specific for these respective enzymes.

7) As previously disclosed, the acrocentric chromosome centromeres can be color stained with colors, such as, for example, blue or red, but not black. Similar accommodations can be made for certain bands on chromosome 10, 12 and Y as well as acrocentric long arm bands to ensure proper identification of all chromosome rearrangements.

8) The slides can be counter-stained with a counter-stain, such as, for example, Methyl Green (Vector Labs) and permanently mounted in a mounting media, such as, for example, permount (Vector Labs). Methyl Green can be used because it will provide exceptional contrast against the three primary colors: Black, Blue and Red.

9) Based on the predetermined proportion of colors at different bands along the length of the individual chromosomes, the admixture of two colors (two enzyme reactions) generates a new detectable color. An example of the color scheme for all bands on all human chromosomes is depicted in FIG. 1.

Microscopic Analysis:

1) Upon color development of individual chromosome bands, the Interphase chromosomes can be observed by using a simple, standard light microscope without any further aid. CCD cameras can be used as a visual aid, however, are not necessary.

2) Starting with slide 1 the color pattern in each Interphase cell can be recorded. Based on the expected normal color pattern from the ideograms, one can determine the normal or abnormal status of the respective acrocentric chromosomes. In general one could score 20 Interphase cells from each well.

3) Repeating the same analysis for the remainder of the chromosomes on slide 2 and 3, i.e., recording the normal and abnormal status of each chromosome using 20 Interphase cells, one can combine the results to get a complete karyotype profile of the individual tested.

4) If additional analysis is indicated, for example, suspicion of mosaicism—normal and abnormal cells, clarification of simple or complex translocations, marker chromosomes or the like, the empty wells on a, such as, Slide # 3 can be used for confirmatory experiments. If needed, an entire extra slide can be used depending on the design of the confirmatory experiment.

5) The banding pattern of any chromosome can be documented by simple digital photography.

6) Simple mosaicism can be easily detected on microscope analysis. Even complex, apparently related clonal mosaicism can be clarified. The following example is illustrative of the clarification procedure according to aspects of the present invention.

Example 10

Karyotype Analysis

As an example, a karyotype with the following results is analyzed: +8/t(9;22)/t(9;22), +8/normal.

In this case of chronic granulocytic leukemia there are two clonal abnormalities: the t(9;22) as discussed supra the characteristic change for this disease. Trisomy 8 (+8) signifies advanced disease progression. However, trisomy 8 can exist alone as an "unrelated" clone. Thus, establishing whether the same clone has both the t(9;22) and +8 is clinically very important.

By way of example, on the first ICP routine reaction, there were 10 cells with t(9;22); 5 cells with +8, 15 cells normal for chromosome 8 and 10 cells normal for chromosomes 9 and 22. As explained everywhere, the clarification of the translocation can be done by the red:blue experiment, where the red:blue juxtaposition indicated a translocation and separate red and blue indicate no translocation. Combining that result with the probe for the chromosome 8 centromere (Black), the results are likely as follows: there were likely 5 cells with t(9;22); 5 cells with t(9;22) and +8; 10 cells normal for chromosomes 8, 9 and 22. These results would clearly indicate that +8 was part of the disease progression, not an isolated event. If it were an isolated event, no cells with the combination result will be observed.

Figure 14:
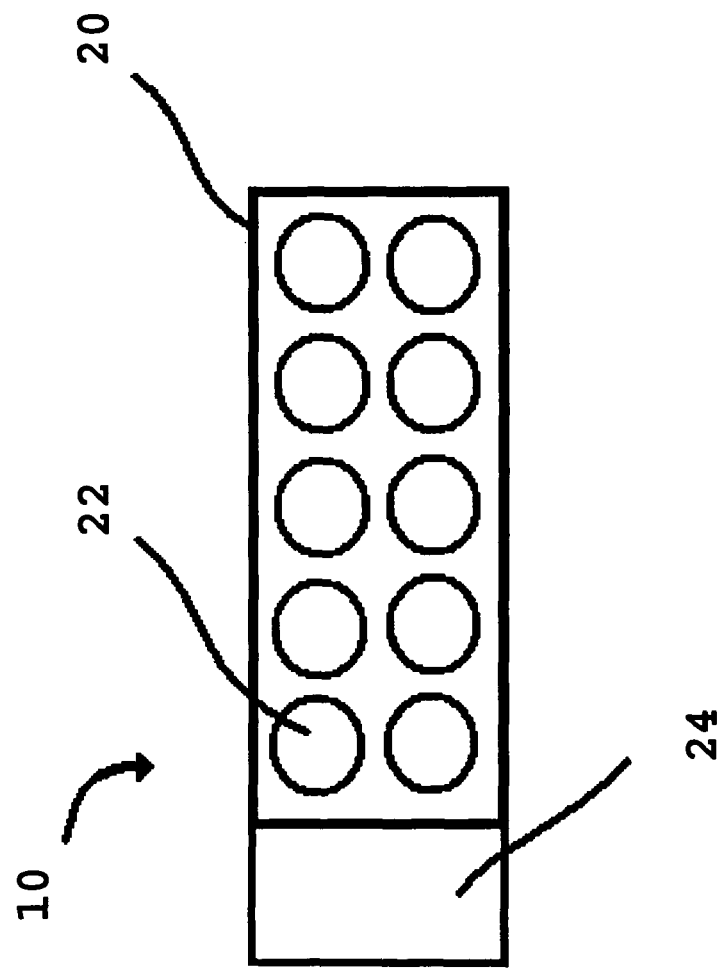
FIG. 14 is a top view of a hybridization slide according to aspects of the present invention.

Referring now to FIG. 14, a hybridization slide according to aspects of the present invention is illustrated and generally referred to by the reference numeral 10. The slide 10 can comprise a body 20, a plurality of wells 22 and an identification label area 24. The body 20 can comprise glass or any other translucent material sufficient for performing hybridization thereon. The wells 22 can comprise areas printed for separating the wells 22 thereon. The wells 22 can also comprise ground out indentations, molded indentations or the like for receiving and hybridizing a sample. The identification label area 24 can comprise a clear area or frosted area for receiving a label or other identification means.

The following tables provide a quick reference to the user to compare results obtained utilizing the techniques disclosed herein to techniques utilizing the Gold Standard G-Banding.

The tables below illustrate the Interphase Chromosome Profile (ICP) banding as compared to the standard G-Banding methods. For ease of reference, the following abbreviations are provided: Q=Long arm; P=Short arm; p=proximal to centromere; q=distal to centromere; Ter=Telomere; ma=Major band; and mi=minor band.

TABLE 1

Chromosome 1

|  | ICP Bands | G-Bands |
|---|---|---|
| Telomere (pter) | Pma5 | P36.3 |
|  | Pmi5 | P36.1d |
|  | Pma4 | P34.3d/p35p |
|  | Pmi4 | P33 |
|  | Pma3 | P31.3d |
|  | Pmi3 | P31.1d |
|  | Pma2 | P31.1p |
|  | Pmi2 | P22.1 |
|  | Pma1 | P13.3d/p21p |
|  | Pmi1 | P13.1 |
| Centromere | Q0 | Q12 |
|  | Qmi1 | Q21.3 |
|  | Qma1 | Q23 |
|  | Qmi2 | Q25 |
|  | Qma2 | Q31d |
|  | Qmi3 | Q32.1 |
|  | Qma3 | Q32.2/q32.3 |
|  | Qmi4 | Q42.1 |
| Telomere (qter) | Qma4 | Q44 |

TABLE 2

Chromosome 2

|  | ICP Bands | G-Bands |
|---|---|---|
| Telomere (pter) | Pma4 | P25/p25.3 |
|  | Pmi4 | P23d/p24p |
|  | Pma3 | P22d/p23p |
|  | Pmi3 | P21d |
|  | Pma2 | P16 |
|  | Pmi2 | P15 |
|  | Pma1 | P13 |
| Centromere | P/q 0 | P/q 0 |
|  | Qmi1 | Q13 |
|  | Qma1 | Q21.1 |
|  | Qmi2 | Q22p |
|  | Qma2 | Q23 |
|  | Qmi3 | Q24.3 |
|  | Qma3 | Q31d/q32.1p |
|  | Qmi4 | Q32.3d/q33p |
|  | Qma4 | Q34d/q35p |
|  | Qmi5 | Q36 |
| Telomere (qter) | Qma5 | Q37.3 |

TABLE 3

Chromosome 3

|  | ICP Bands | G-Bands |
|---|---|---|
| Telomere (pter) | Pma4 | p26 |
|  | Pmi4 | P24d/p25p |
|  | Pma3 | P24p |
|  | Pmi3 | P21d/p22p |
|  | Pma2 | P21.3p |
|  | Pmi2 | P14.3 |
|  | Pma1 | P13/p14.1p |
|  | Pmi1 | p12 |
| Centromere | p/q 0 |  |
|  | Qmi1 | Q13.1 |
|  | Qma1 | q13.3 |
|  | Qmi2 | q21d |
|  | Qma2 | Q23/q24p |
|  | Qmi3 | Q25.1 |
|  | Qma3 | Q26.2 |
|  | Qmi4 | q27 |
| Telomere (qter) | Qma4 | q29 |

TABLE 4

Chromosome 4

|  | ICP Bands | G-Bands |
|---|---|---|
| Telomere (pter) | Pma2 | p16d |
|  | Pmi2 | P15.3 |
|  | Pma1 | P15.1 |
|  | Pmi1 | P14p/p13d |
| Centromere | p/q 0 |  |
|  | Qmi1 | Q13.2 |
|  | Qma1 | Q21.2 |
|  | Qmi2 | q22d |
|  | Qma2 | Q25/q24d |
|  | Qmi3 | Q26/q26d |
|  | Qma3 | q28p |
|  | Qmi4 | Q31.1 |
|  | Qma4 | Q31.3/q32p |
|  | Qmi5 | q33 |
| Telomere (qter) | Qma5 | q35 |

TABLE 5

Chromosome 5

|  | ICP Bands | G-Bands |
|---|---|---|
| Telomere (pter) | Pma2 | P15.3 |
|  | Pmi2 | P15.2/p15.1 |
|  | Pma1 | p14 |
|  | Pmi1 | P13.2 |
| Paracentromere | Q0 | Q11.2 |
|  | Qmi1 | Q12d/q13.1 |
|  | Qma1 | Q13.3/q14p |
|  | Qmi2 | q15 |
|  | Qma2 | q21d |
|  | Qmi3 | Q23.1 |
|  | Qma3 | Q23.3/q31.1 |
|  | Qmi4 | Q31.3 |
|  | Qma4 | Q32/q33.1 |
|  | Qmi5 | q34 |
| Telomere (qter) | Qma5 | Q35.2/q35.3 |

TABLE 6

Chromosome 6

| | ICP Bands | G-Bands |
|---|---|---|
| Telomere (pter) | Pma3 | p25 |
| | Pmi3 | p23d |
| | Pma2 | P22/p22.2 |
| | Pmi2 | P21.3p |
| | Pma1 | P21.2 |
| Centromere | p/q 0 | |
| | Qmi1 | q13 |
| | Qma1 | Q16.1/q15 |
| | Qmi2 | q21p |
| | Qma2 | Q22.1 |
| | Qmi3 | Q22.3d |
| | Qma3 | q24 |
| | Qmi4 | Q25.3 |
| Telomere (qter) | Qma4 | q27 |

TABLE 7

Chromosome 7

| | ICP Bands | G-Bands |
|---|---|---|
| Telomere (pter) | Pma3 | P22 |
| | Pmi3 | P21d |
| | Pma2 | P21p/p15.3 |
| | Pmi2 | P15.1 |
| | Pma1 | P14p/p13d |
| | Pmi1 | P12 |
| Centromere | p/q 0 | |
| | Qmi1 | Q11.23p |
| | Qma1 | Q21.1 |
| | Qmi2 | Q21.3/q22p |
| | Qma2 | Q31.1 |
| | Qmi3 | Q31.3 |
| | Qma3 | Q32 |
| | Qmi4 | Q35 |
| Telomere (qter) | Qma4 | q36 |

TABLE 8

Chromosome 8

| | ICP Bands | G-Bands |
|---|---|---|
| Telomere (pter) | Pma2 | P23.2/p23.3 |
| | Pmi2 | P22d |
| | Pma1 | P21.2 |
| | Pmi1 | P12 |
| Centromere | p/q 0 | |
| | Qmi1 | Q12 |
| | Qma1 | Q13d/q21.1p |
| | Qmi2 | Q21.2 |
| | Qma2 | Q21.3d/q22.1 |
| | Qmi3 | Q22.3 |
| | Qma3 | Q23d |
| | Qmi4 | Q24.1 |
| Telomere (qter) | Qma4 | Q24.3 |

TABLE 9

Chromosome 9

| | ICP Bands | G-Bands |
|---|---|---|
| Telomere (pter) | Pma2 | P24 |
| | Pmi2 | P23p |
| | Pma1 | P21 |
| | Pmi1 | P13p |
| Paracentromere | Q0 | Q12 |
| | Qmi1 | Q21.2 |

TABLE 9-continued

Chromosome 9

| | ICP Bands | G-Bands |
|---|---|---|
| | Qma1 | Q22.1 |
| | Qmi2 | Q22.3 |
| | Qma2 | Q31d/q32 |
| | Qmi3 | Q34. |
| Telomere (qter) | Qma3 | Q34.2/q34.3 |

TABLE 10

Chromosome 10

| | ICP Bands | G-Bands |
|---|---|---|
| Telomere | Pma2 | P15 |
| | Pmi2 | P14p |
| | Pma1 | P12.3d/p13p |
| | Pmi1 | P11.2d |
| Centromere | p/q 0 | |
| | Qmi1 | Q21.1p |
| | Qma1 | Q21.3d |
| | Qmi2 | Q22.1 |
| | Qma2 | Q22.3d/q23.1p |
| | Qmi3 | Q23.3 |
| | Qma3 | Q24.3d/q25.1p |
| | Qmi4 | Q25.3 |
| Telomere (qter) | Qma4 | Q26.2/q26.3 |

TABLE 11

Chromosome 11

| | ICP Bands | G-Bands |
|---|---|---|
| Telomere (pter) | Pma3 | P15.5 |
| | Pmi3 | P15.2/p15.3 |
| | Pma2 | P14d |
| | Pmi2 | P14p |
| | Pma1 | P13/p12d |
| | Pmi1 | P11.2 |
| Centromere | p/q 0 | |
| | Qmi1 | Q12d |
| | Qma1 | Q13.3/q13.4 |
| | Qmi2 | Q14.1 |
| | Qma2 | Q21 |
| | Qmi3 | Q22.3 |
| | Qma3 | Q23.2/q23.3p |
| | Qmi4 | Q23.3d |
| Telomere (qter) | Qma4 | q25 |

TABLE 12

Chromosome 12

| | ICP Bands | G-Bands |
|---|---|---|
| Telomere (pter) | Pma2 | P13.3 |
| | Pmi2 | P13.1 |
| | Pma1 | P12.2/p12.3p |
| | Pmi1 | P11.2 |
| Centromere | p/q 0 | |
| | Qmi1 | Q13.1p |
| | Qma1 | Q13.3/q14p |
| | Qmi2 | Q15 |
| | Qma2 | Q21.3p |
| | Qmi3 | Q22 |
| | Qma3 | Q23d |
| | Qmi4 | Q24.1d |
| Telomere (qter) | Qma4 | Q24.32/q24.33 |

TABLE 13

Chromosome 13

| | ICP Bands | G-Bands |
|---|---|---|
| Centromere | Q0 | |
| | Qmi1 | Q12.3 |
| | Qma1 | Q14.2 |
| | Qmi2 | Q21.1 |
| | Qma2 | Q21.3 |
| | Qmi3 | Q22 |
| | Qma3 | Q31 |
| | Qmi4 | Q32d |
| Telomere (qter) | Qma4 | q34 |

TABLE 14

Chromosome 14

| | ICP Bands | G-Bands |
|---|---|---|
| Centromere | Q0 | |
| | Qmi1 | Q12p |
| | Qma1 | Q13d |
| | Qmi2 | Q21/q21d |
| | Qma2 | Q22d/q23 |
| | Qmi3 | Q24.1 |
| | Qma3 | Q24.3 |
| | Qmi4 | Q31d |
| Telomere (qter) | Qma4 | Q32.2/q32.3 |

TABLE 15

Chromosome 15

| | ICP Bands | G-Bands |
|---|---|---|
| Centromere | Q0 | |
| | Qmi1 | Q13 |
| | Qma1 | Q14d/q15p |
| | Qmi2 | Q21.1 |
| | Qma2 | Q21.3d/q22.1 |
| | Qmi3 | Q22.3 |
| | Qma3 | Q24 |
| | Qmi4 | q25d |
| Telomere (qter) | Qma4 | Q26.2/q26.3 |

TABLE 16

Chromosome 16

| | ICP Bands | G-Bands |
|---|---|---|
| Telomere (pter) | Pma2 | P13.3 |
| | Pmi2 | P13.1 |
| | Pma1 | P12p |
| | Pmi1 | P11.2 |
| Paracentromere | Q0 | Q11.2 |
| | Qmi1 | Q13 |
| | Qma1 | Q21d/q22p |
| | Qmi2 | Q22d/q23p |
| Telomere (qter) | Qma2 | q24 |

TABLE 17

Chromosome 17

| | ICP Bands | G-Bands |
|---|---|---|
| Telomere (pter) | Pma2 | P13d |
| | Pmi2 | P13p/p12d |

TABLE 17-continued

Chromosome 17

| | ICP Bands | G-Bands |
|---|---|---|
| | Pma1 | P12p |
| | Pmi1 | P11.2 |
| Centromere | p/q 0 | |
| | Qmi1 | Q11.2d/q12p |
| | Qma1 | Q21.2/q21.3p |
| | Qmi2 | Q21.3d/q22p |
| | Qma2 | Q22d/q23p |
| | Qmi3 | Q24 |
| Telomere (qter) | Qma3 | q25 |

TABLE 18

Chromosome 18

| | ICP Bands | G-Bands |
|---|---|---|
| Telomere (pter) | Pma1 | P11.3/p11.32 |
| | Pmi1 | P11.2 |
| Centromere | p/q 0 | |
| | Qmi1 | Q11.2d |
| | Qma1 | Q12.3d |
| | Qmi2 | Q21.1 |
| | Qma2 | Q21.3 |
| | Qmi3 | Q22 |
| Telomere (qter) | Qma3 | q23 |

TABLE 19

Chromosome 19

| | ICP Bands | G-Bands |
|---|---|---|
| Telomere (pter) | Pma2 | P13.3d |
| | Pmi2 | P13.3p |
| | Pma1 | P13.2 |
| | Pmi1 | P13.1p |
| Paracentromere | Qo | Q12 |
| | Qmi1 | Q13.1 |
| | Qma1 | Q13.1d/q13.2p |
| | Qmi2 | Q13.3 |
| Telomere (qter) | Qma2 | Q13.4 |

TABLE 20

Chromosome 20

| | ICP Bands | G-Bands |
|---|---|---|
| Telomere (pter) | Pma2 | P13d |
| | Pmi2 | P13p/p12d |
| | Pma1 | P12p/p11.2d |
| Centromere | p/q 0 | |
| | Qmi1 | Q11.2 |
| | Qma1 | Q12 |
| | Qmi2 | Q13.1 |
| Telomere (qter) | Qma2 | Q13.3 |

TABLE 21

Chromosome 21

| | ICP Bands | G-Bands |
|---|---|---|
| Centromere | Q0 | |
| | Qmi1 | Q21p |

TABLE 21-continued

Chromosome 21

| | ICP Bands | G-Bands |
|---|---|---|
| | Qma1 | Q21d |
| | Qmi2 | Q22.1 |
| Telomere | Qma2 | Q22.3 |

TABLE 22

Chromosome 22

| | ICP Bands | G-bands |
|---|---|---|
| Centromere | Q0 | |
| | Qmi1 | Q11.2 |
| | Qma1 | Q12.3/q13.1p |
| | Qmi2 | Q13.1d |
| Telomere (qter) | Qma2 | Q13.3 |

TABLE X

Chromosome X

| | ICP Bands | G-bands |
|---|---|---|
| Telomere (pter) | Pma3 | P22.3 |
| | Pmi3 | P22.1d |
| | Pma2 | P22.1p/p21.3 |
| | Pmi2 | P21.1 |
| | Pma1 | P11.4/p11.3 |
| | Pmi1 | P11.23 |
| Centromere | p/q 0 | |
| | Qmi1 | P13p |
| | Qma1 | P13d/p21.1p |
| | Qmi2 | Q21.3d |
| | Qma2 | Q22 |
| | Qmi3 | Q25d/q26p |
| | Qmi4 | Q27p |
| Telomere (qter) | Qma4 | q28 |

TABLE Y

Chromosome Y

| | ICP Bands | G-Bands |
|---|---|---|
| Telomere (pter) | Pma1 | P11.3/p11.2d |
| | Pmi1 | P11.2p |
| Centromere | p/q 0 | |
| | Qmi1 | Q11.221 |
| | Qma1 | Q11.222/q11.223 |
| | Qmi2 | Q11.23 |
| Q Heterochromatin | Qma2 | q12 |

Inasmuch as the preceding disclosure presents the best mode devised by the invention for practicing the invention and is intended to enable one skilled in the pertinent art to carry it out, it is apparent that methods incorporating modifications and variations will be obvious to those skilled in the art. As such, it should not be construed to be limited thereby but should include such aforementioned obvious variations and be limited only by the spirit and scope of the following claims.

REFERENCES

Babu V R and Wiktor A. A fluorescence in situ hybridization technique for retrospective cytogenetic analysis. 1991, 57:16-17.

Berend Sa, Horwitz J, McCaskill C, Shaffer L G. Identification of uniparental disomy following prenatal detection of Robertsonian translocations and isochromosomes. Am J Hum Genet. 2000, 66(6):1787-93.

Chudoba I, Plesch A, Lorch T et al., High resolution multicolor-banding: a new technique for refined FISH analysis of human chromosomes. Cytogenet Cell Genet. 1999, 84(3-4):156-160.

Craig J M, Kraus J, Cremer T. Removal of repetitive sequences from FISH probes using PCR-assisted affinity chromatography. Hum Genet. September 1997; 100(3-4): 472-6.

Kakazu N, Bar-Am I, Hada S et al., A new chromosome banding technique, spectral color banding (SCAN), for full characterization of chromosomal abnormalities. Genes Chromosomes Cancer. August 2003, 37(4):412-16.

Lemke J, Claussen J, Michel S et al., The DNA-based structure of human chromosome 5 in Interphase. Am J Hum Genet. 2002, 71(5):1051-59.

Liehr T, Heller A, Starke H et al., Microdissection based high resolution multicolor banding for all 24 human chromosomes. Int J Mol Med. April 2002; 9(4):335-9.

Muller S, Rocchi M, Ferguson-Smith M A et al., Toward a multicolor chromosome bar code for the entire human karyotype by fluorescence in situ hybridization. Hum Genet. 1997, 100:271-8.

Muller S, O'Brien P C, Ferguson-Smith M A et al., Cross species color segmenting: a novel tool in human karyotype analysis. Cytometry. 1998, 33:445-52.

Silverstein S, Lerer I, Sagi M, Frumkin A, Ben-Neriah Z, Abeliovich D. Uniparental disomy in fetuses diagnosed with balanced Robertsonian translocations: risk estimate. Prenat Diagn. 2002, 22(8):649-51.

Telenius H, Carter N P, Bebb C E et al., Degenrative oligonucleotide-primed PCR: general amplification of target DNA by a single degenerate primer. Genomics. July 1992; 13(3):718-25.

Davidson J M, Morgan T W, His B L et al., Substracted, Unique-Sequence, In Situ Hybridization. Am J Pathol. 1998, 153:1401-09

Pinkel D, Straume T, Gray J W. Cytogenetic analysis using quantitative, high-sensitivity, fluorescence hybridization. Proc Natl Acad Sci, USA. 1986, 83:2934-38.

Meltzer P S, Guan X Y, Burgess A et al., Rapid generation of region specific probes by chromosome microdissection and their application. Nature Genetics, April 1992; 1(1): 24-8.

Hu L, Sham J, Tjia W et al., Generation of a complete set of human telomeric band painting probes by chromosome microdissection. Genomics, February 2004; 83(2):298-302.

Meltzer P and Bittner M. Chromosome Microdissection in Current Protocols in Human Genetics, Unit 4.8, 2001 John Wiley & Sons, Inc.

Human Chromosomes—Manual of Basic Techniques. Verma R and Babu A. Pergamon Press, New York. 1989.

ISCN (1995): An International System for Human Cytogenetic Nomenclature, Mitelman F (ed); S. Karger, Basel, 1995.

The AGT Cytogenetics Manual. $3^{rd}$ ed. Barch M J, Knutsen J L, Spurbeck (ed). Lippincot-Raven, Philadelphia. 1997. The Principles of Clinical Cytogenetics. Gersen S and Keagle M, (ed). Human Press, Totowa, N.J. 2004.

I claim:

1. A method for generating an interphase chromosome profile comprising:
   obtaining a sample containing cells having at least one interphase chromosome for profiling;
   obtaining a plurality of different species specific, chromosome specific, and location specific DNA probes, wherein said DNA probes contain different antibody-specific labels and are capable of marking a normal control chromosome of the at least one interphase chromosome for profiling at substantially equidistant locations on the normal control chromosome;
   hybridizing said sample with said DNA probes;
   detecting the hybridization of said DNA probes to the at least one interphase chromosome for profiling using a plurality of different specific enzymes, a plurality of different specific antibodies, and different specific substrates, wherein said plurality of different specific enzymes and said plurality of different specific antibodies form a plurality of different specific enzyme-antibody conjugates, each of said enzyme-antibody conjugates comprises at least one of said specific antibodies and at least one of said specific enzymes and wherein each of said specific antibodies binds to one of said antibody specific labels that is attached to one of said specific DNA probes and wherein each of said specific enzymes reacts with its specific substrate from said specific substrates such that mixed differential major color bands are produced on the at least one interphase chromosome for profiling; and
   comparing said mixed differential major color bands on the at least one interphase chromosome for profiling with mixed differential major color bands on the normal control chromosome by visual analysis and determining the interphase chromosome profile of the at least one interphase chromosome for profiling, wherein said mixed differential major color bands on said normal control chromosome are generated by hybridizing said normal control chromosome with said DNA probes and detecting the hybridization of said DNA probes to said normal control chromosome using said enzyme-antibody conjugates and said specific substrates, and each adjacent band of said mixed differential major color bands on said normal control chromosome are spaced at substantially the same distance.

2. The method of claim 1 further comprising creating differential minor bands among said mixed differential major color bands on the at least one interphase chromosome for profiling using an additional differential stain.

3. The method of claim 2 wherein said additional differential stain comprises a black pigment.

4. The method of claim 2 wherein said mixed differential major color bands and said differential minor bands on the at least one interphase chromosome for profiling are present in a ratio of 1:1.

5. The method of claim 2 wherein the at least one interphase chromosome for profiling comprises a long arm and a short arm and wherein the thicknesses of said differential minor bands of said long arm and said short arm are different.

6. The method of claim 1 wherein said hybridization is in situ hybridization wherein the sample is on a slide.

7. The method of claim 6 wherein said slide comprises a series of wells for receiving, hybridizing and analyzing the at least one interphase chromosome for profiling.

8. The method of claim 1 wherein said visual analysis comprises utilizing a light microscope.

9. The method of claim 1 wherein said visual analysis comprises utilizing a CCD camera.

10. The method of claim 1 wherein the origin of said sample is selected from the group consisting of amniotic fluid, chorionic villi, peripheral blood, plural fluid, bone marrow, tumor tissue, and products of conception.

11. The method of claim 2 wherein said visual analysis is used to detect a suspected chromosome abnormality on the at least one interphase chromosome for profiling by comparing the mixed differential major color bands and differential minor bands on the at least one interphase chromosome for profiling with the mixed differential major color bands and differential minor bands on the normal control chromosome wherein the differential minor bands on the normal control chromosome are generated by staining the normal control chromosome using said additional differential stain.

12. The method of claim 11 wherein said chromosome abnormality is a structural chromosome abnormality or a numerical chromosome abnormality.

13. The method of claim 11 wherein said chromosome abnormality is selected from the group consisting of a chromosome translocation, a chromosome deletion, a chromosome inversion, a trisomy, and a chromosomal amplification.

14. The method of claim 2 wherein the interphase chromosome profile is used to produce a complete karyotype when the sample is from a human.

15. A method of colorimetric in situ hybridization comprising the steps of:
   obtaining a sample containing cells having at least one chromosome for profiling;
   obtaining a plurality of different species specific, chromosome specific, and location specific DNA probes, wherein said DNA probes contain different antibody-specific labels and are capable of marking the at least one chromosome for profiling at substantially equidistant locations on the at least one chromosome for profiling;
   in situ hybridizing said sample with said DNA probes; and
   detecting the hybridization of said DNA probes to the at least one chromosome for profiling using a plurality of different specific enzymes, a plurality of different specific antibodies, and different specific substrates, wherein said plurality of different specific enzymes and said plurality of different specific antibodies form a plurality of different specific enzyme-antibody conjugates, each of said enzyme-antibody conjugates comprises at least one of said specific antibodies and at least one of said specific enzymes and wherein each of said specific antibodies binds to one of said antibody specific labels that is attached to one of said specific DNA probes and wherein each of said specific enzymes reacts with its specific substrate from said specific substrates such that mixed differential major color bands are produced on the at least one chromosome for profiling and each adjacent band of said mixed differential major color bands on the at least one chromosome for profiling are spaced at substantially the same distance.

16. The method of claim 15 further comprising creating differential minor bands among said mixed differential major color bands on the at least one chromosome for profiling using an additional differential stain.

17. The method of claim 16 wherein said additional differential stain comprises a black pigment.

18. The method of claim 16 wherein said mixed differential major color bands and said differential minor bands on the at least one chromosome for profiling are present in a ratio of 1:1.

19. The method of claim 16 wherein the at least one chromosome for profiling comprises a long arm and a short arm and wherein the thicknesses of said differential minor bands of said long arm and said short arm are different.

20. The method of claim 15 wherein said in situ hybridization occurs on a slide.

21. The method of claim 20 wherein said slide comprises a series of wells for receiving, hybridizing and analyzing the at least one chromosome for profiling.

22. A method of visually determining whether a Robertsonian translocation has occurred among acrocentric chromosomes in a human sample comprising the steps of:
obtaining a human sample containing cells having acrocentric chromosomes for profiling;
obtaining a plurality of different chromosome specific and location specific human DNA probes, wherein said DNA probes contain different antibody-specific labels and are capable of marking normal control acrocentric chromosomes at substantially equidistant locations on each of said normal acrocentric chromosomes;
hybridizing said sample with said DNA probes;
detecting the hybridization of said DNA probes to acrocentric chromosomes for profiling using a plurality of different specific enzymes, a plurality of different specific antibodies, and different specific substrates, wherein said plurality of different specific enzymes and said plurality of different specific antibodies form a plurality of different specific enzyme-antibody conjugates, each of said enzyme-antibody conjugates comprises at least one of said specific antibodies and at least one of said specific enzymes and wherein each of said specific antibodies binds to one of said antibody specific labels that is attached to one of said specific DNA probes and wherein each of said specific enzymes reacts with its specific substrate from said specific substrates such that mixed differential major color bands are produced on each of said acrocentric chromosomes; and
comparing said mixed differential major color bands on each of said acrocentric chromosomes for profiling with mixed differential major color bands on the normal control acrocentric chromosomes by visual analysis and determining whether a Robertsonian translocation has occurred among said acrocentric chromosomes for profiling, wherein said mixed differential major color bands on said normal control acrocentric chromosomes are generated by hybridizing said normal control acrocentric chromosomes with said DNA probes and detecting the hybridization of said DNA probes to said normal control acrocentric chromosomes using said enzyme-antibody conjugates and said specific substrates, and each adjacent band of said mixed differential major color bands on each of said normal control acrocentric chromosomes are spaced at substantially the same distance.

23. The method of claim 22 further comprising creating differential minor bands among said mixed differential major color bands on each of said acrocentric chromosomes for profiling using an additional differential stain.

24. The method of claim 23 wherein said additional differential stain comprises a black pigment.

25. The method of claim 23 wherein said mixed differential major color bands and said differential minor bands on each of said acrocentric chromosomes for profiling are present in a ratio of 1:1.

26. The method of claim 22 wherein said hybridization is in situ hybridization wherein the sample is on a slide.

27. The method of claim 26 wherein said slide comprises a series of wells for receiving, hybridizing and analyzing said acrocentric chromosomes for profiling.

28. The method of claim 22 wherein said visual analysis comprises utilizing a light microscope.

29. The method of claim 22 wherein said visual analysis comprises utilizing a CCD camera.

30. The method of claim 22 wherein the origin of said human sample is selected from the group consisting of amniotic fluid, chorionic villi, peripheral blood, plural fluid, bone marrow, tumor tissue, and products of conception.

31. A method of verifying the presence of a marker chromosome in a sample comprising the steps of:
obtaining a sample containing cells having a chromosomal material suspected of containing partial chromosomes for analysis;
obtaining a plurality of different species specific, chromosome specific, and location specific DNA probes, wherein said DNA probes contain different antibody-specific labels and are capable of marking normal control chromosomes of said partial chromosomes at substantially equidistant locations on each of said normal control chromosomes;
hybridizing said sample with said DNA probes; and
detecting the hybridization of said DNA probes to said chromosomal material suspected of containing partial chromosomes using a plurality of different specific enzymes, a plurality of different specific antibodies, and different specific substrates, wherein said plurality of different specific enzymes and said plurality of different specific antibodies form a plurality of different specific enzyme-antibody conjugates, each of said enzyme-antibody conjugates comprises at least one of said specific antibodies and at least one of said specific enzymes and wherein each of said specific antibodies binds to one of said antibody specific labels that is attached to one of said specific DNA probes and wherein each of said specific enzymes reacts with its specific substrate from said specific substrates such that mixed differential major color bands are produced on said chromosomal material suspected of containing partial chromosomes; and
comparing said mixed differential major color bands on said chromosomal material suspected of containing partial chromosomes with mixed differential major color bands on said normal control chromosomes by visual analysis and verifying whether said chromosomal material contains said partial chromosomes, wherein the presence of said partial chromosomes in said chromosomal material indicates the presence of said marker chromosome in the sample, said mixed differential major color bands on said normal control chromosomes are generated by hybridizing said normal control chromosomes with said DNA probes and detecting the hybridization of said DNA probes to said normal control chromosomes using said enzyme-antibody conjugates and said specific substrates, and each adjacent band of said mixed differential major color bands on each of said normal control chromosomes are spaced at substantially the same distance.

32. The method of claim 31 further comprising creating differential minor bands among said major color bands on each chromosome of said chromosomal material suspected of containing partial chromosomes.

33. The method of claim 32 wherein said additional differential stain comprises a black pigment.

34. The method of claim 32 wherein said mixed differential major color bands and said differential minor bands on each chromosome of said chromosomal material suspected of containing partial chromosomes are present in a ratio of 1:1.

35. The method of claim 32 wherein each chromosome in said chromosomal material comprises a long arm and a short arm and wherein the thicknesses of said differential minor bands of said long arm and said short arm are different.

36. The method of claim 31 wherein said hybridization is in situ hybridization wherein the sample is on a slide.

37. The method of claim 36 wherein said slide comprises a series of wells for receiving, hybridizing and analyzing said chromosomal material suspected of containing partial chromosomes.

38. The method of claim 31 wherein said visual analysis comprises utilizing a light microscope.

39. The method of claim 31 wherein said visual analysis comprises utilizing a CCD camera.

40. The method of claim 31 wherein the origin of said sample is selected from the group consisting of amniotic fluid, chorionic villi, peripheral blood, plural fluid, bone marrow, tumor tissue, and products of conception.

\* \* \* \* \*